US010512740B2

(12) United States Patent
Herder et al.

(10) Patent No.: US 10,512,740 B2
(45) Date of Patent: Dec. 24, 2019

(54) INHALATION DEVICE FOR POWDERED DRUGS

(71) Applicant: Almirall, S.A., Barcelona (ES)

(72) Inventors: Martin Herder, Bad Homburg (DE); Gerhard Ludanek, Bad Homburg (DE); Ingo Mett, Bad Homburg (DE); Joachim Schmidt, Bad Homburg (DE)

(73) Assignee: ASTRAZENECA AB, Sodertalje (SE)

( * ) Notice: Subject to any disclaimer, the term of this patent is extended or adjusted under 35 U.S.C. 154(b) by 953 days.

(21) Appl. No.: 14/373,572

(22) PCT Filed: Jan. 17, 2013

(86) PCT No.: PCT/EP2013/000128
§ 371 (c)(1),
(2) Date: Jul. 21, 2014

(87) PCT Pub. No.: WO2013/107642
PCT Pub. Date: Jul. 25, 2013

(65) Prior Publication Data
US 2014/0373838 A1 Dec. 25, 2014

Related U.S. Application Data

(60) Provisional application No. 61/589,575, filed on Jan. 23, 2012.

(30) Foreign Application Priority Data

Jan. 20, 2012 (EP) .................................... 12000355

(51) Int. Cl.
*A61M 15/00* (2006.01)
(52) U.S. Cl.
CPC .... *A61M 15/0073* (2014.02); *A61M 15/0026* (2014.02); *A61M 15/0065* (2013.01);
(Continued)

(58) Field of Classification Search
CPC ............... G06M 1/00; A61M 15/00; A61M 15/0001–001; A61M 15/0013–0026;
(Continued)

(56) References Cited

U.S. PATENT DOCUMENTS 5,840,279 A 11/1998 Narodylo et al.
2004/0069301 A1* 4/2004 Bacon ............... A61M 15/0091
128/200.23

(Continued)

FOREIGN PATENT DOCUMENTS

AU 2009200071 B2 2/2009
EP 1616592 A1 1/2006
(Continued)

OTHER PUBLICATIONS

English language PCT International Search Report and Written Opinion dated Jul. 31, 2013, received in corresponding PCT Application No. PCT/EP13/00128, 17 pgs.

(Continued)

*Primary Examiner* — Samchuan C Yao
*Assistant Examiner* — Ned T Heffner
(74) *Attorney, Agent, or Firm* — Grossman, Tucker, Perreault & Pfleger, PLLC

(57) ABSTRACT

The invention relates to an inhalation device for powdered drugs to be received by a patient by an inhalation-caused air stream, comprising at least one powder reservoir, metering means for repeatedly metering a powder dose from the reservoir, a transportation mechanism for moving said metering means from a filling position for receiving a powder dose into an emptying position for releasing said powder dose into a powder channel, at least one activating device for manual operation by the patient, said activating device being operatively connected to said transportation mechanism such that upon operation a single powder dose is (Continued)

Figure 1:
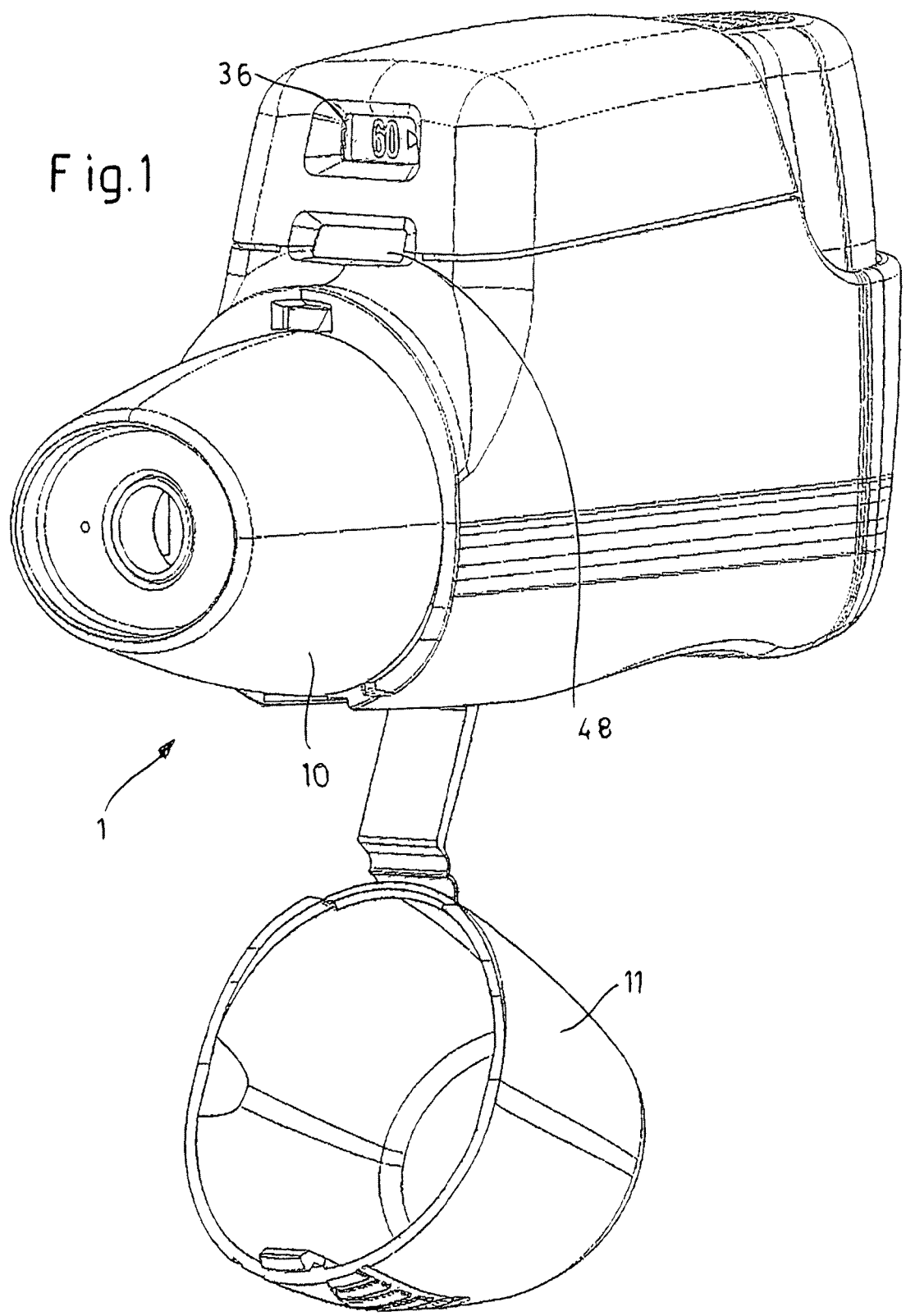

being metered, said activating device comprising a dosage key (5) acting on said transportation mechanism when pressed by the patient. The inhalation device further comprises an advancing mechanism for advancing a counter means each time the inhalation device has been activated by the patient so that a powder dose has been released into the powder channel. The counter means comprises a mechanical index coupled to a locking mechanism blocking the dosage key (5) and/or the activating device and/or the transportation mechanism after a predetermined number of metering cycles after detection of the index. Moreover, the locking mechanism includes a locking lever (7) for positive engagement with the dosage key (5) and/or the activating device and/or the transportation mechanism in the blocked condition. The inhalation device (1) is characterized in that the locking lever includes signaling means integrally formed therewith engaging the index after said predetermined number of metering cycles.

15 Claims, 25 Drawing Sheets

(52) U.S. Cl.
CPC .... *A61M 15/0081* (2014.02); *A61M 15/0091* (2013.01); *A61M 15/0093* (2014.02); *A61M 15/0095* (2014.02); *A61M 15/0096* (2014.02); *A61M 2202/064* (2013.01); *A61M 2205/584* (2013.01); *A61M 2206/16* (2013.01)

(58) Field of Classification Search
CPC ... A61M 15/0028–0038; A61M 15/004–0043; A61M 15/0045–0051; A61M 15/0056; A61M 15/006; A61M 15/0065; A61M 15/0068–0083; A61M 15/0086–0088; A61M 15/0091–0098; A61M 15/06; A61M 15/08–085; A61M 2202/064; A61J 1/2006–2017; A61K 9/14
See application file for complete search history.

(56) References Cited

U.S. PATENT DOCUMENTS

| | | | |
|---|---|---|---|
| 2004/0089298 A1* | 5/2004 | Haikarainen | A61M 15/0065 128/203.15 |
| 2006/0037612 A1* | 2/2006 | Herder | A61M 15/0065 128/203.15 |
| 2010/0083963 A1 | 4/2010 | Wharton et al. | |

FOREIGN PATENT DOCUMENTS

| EP | 1616592 A1 | 9/2010 |
| WO | 9936115 A2 | 7/1999 |
| WO | 2005028006 A1 | 3/2005 |
| WO | 2006106367 A1 | 10/2006 |
| WO | 2008077623 A1 | 7/2008 |

OTHER PUBLICATIONS

English translation of Mexican Office Action dated Nov. 10, 2017, received in related Mexican Application No. MX/a/2014/008788, 4 pgs.
English translation of Korean Notice of Allowance dated Aug. 30, 2019, received in related Korean Application No. 10-2014-7023018.

* cited by examiner

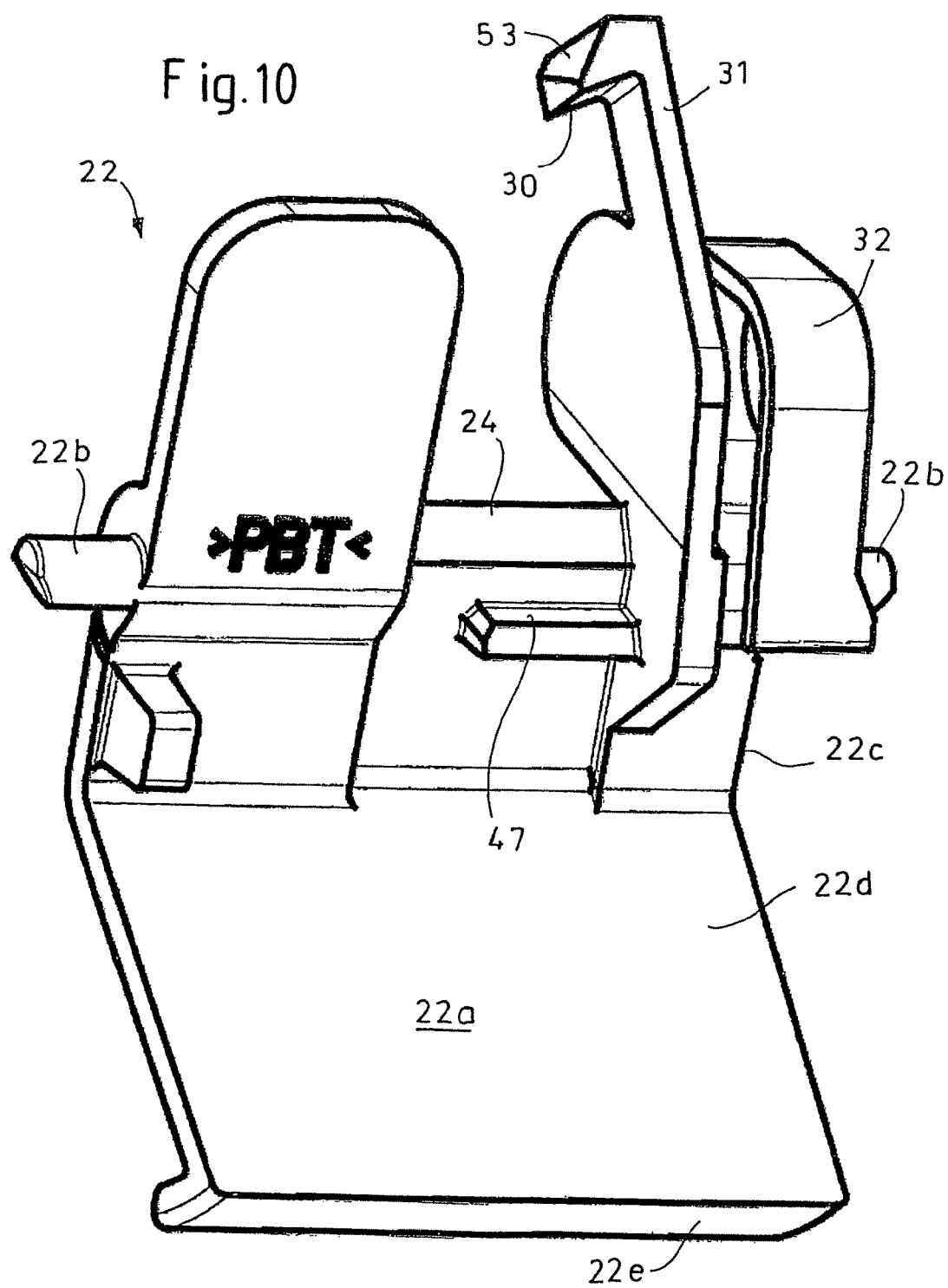

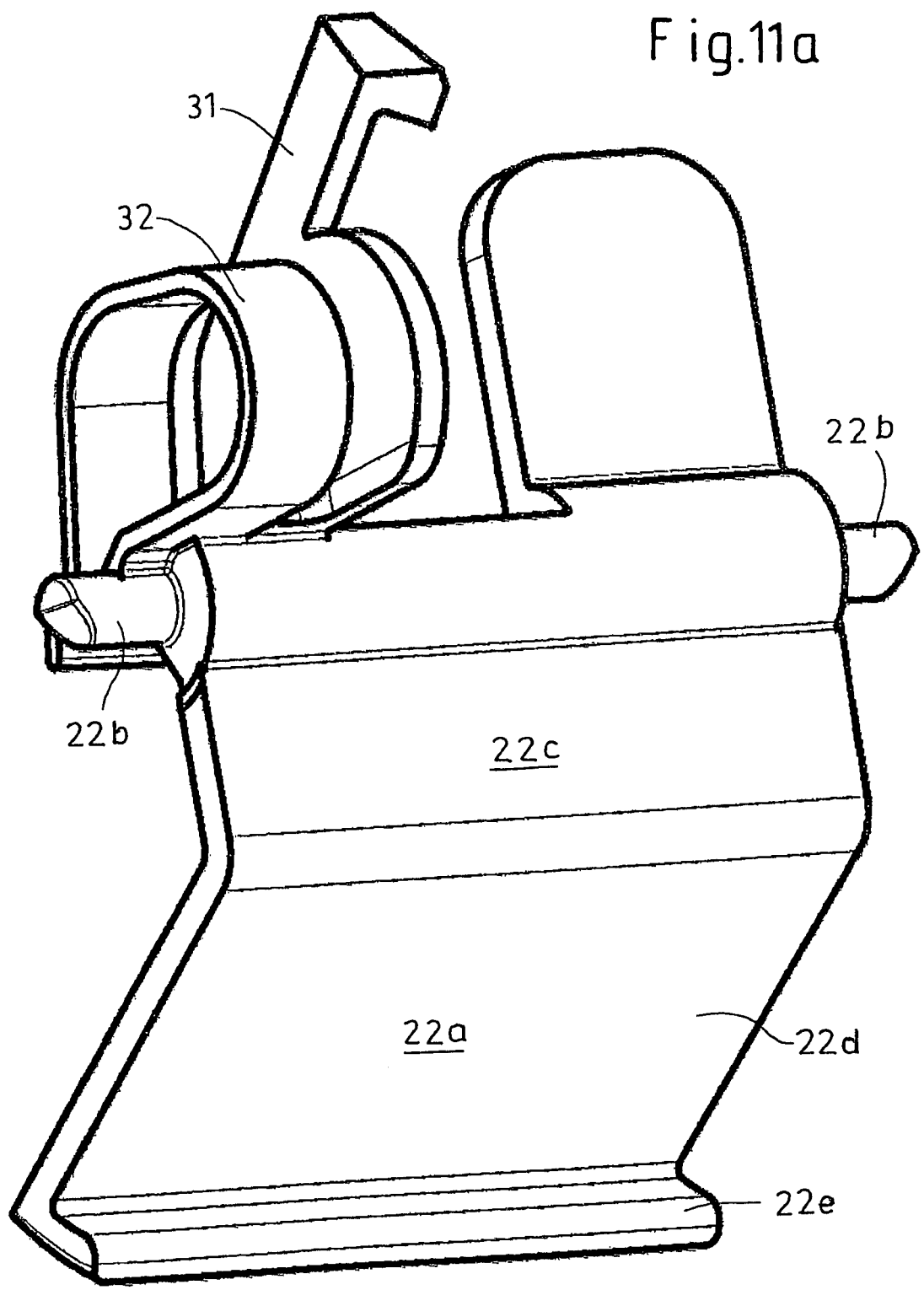

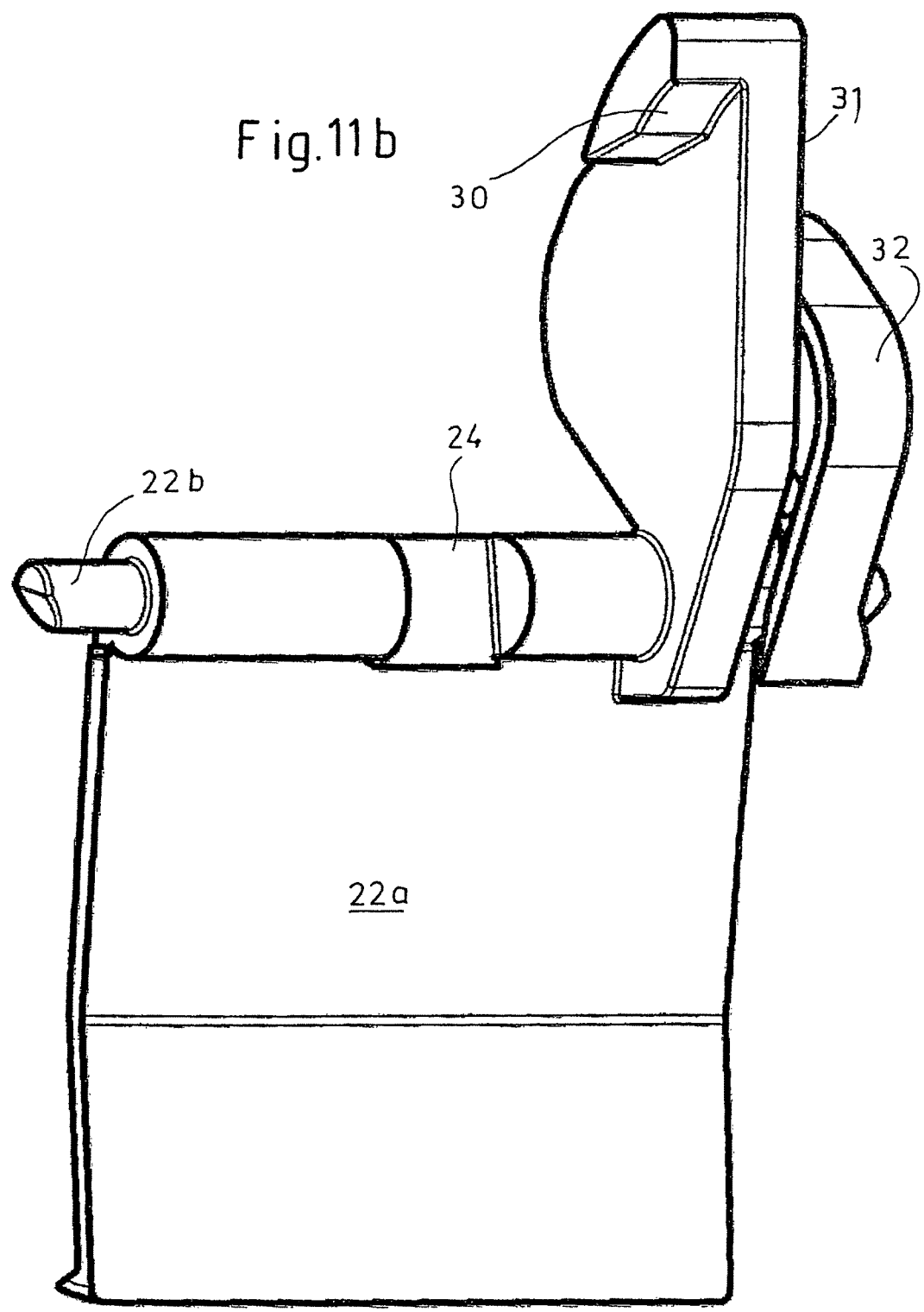

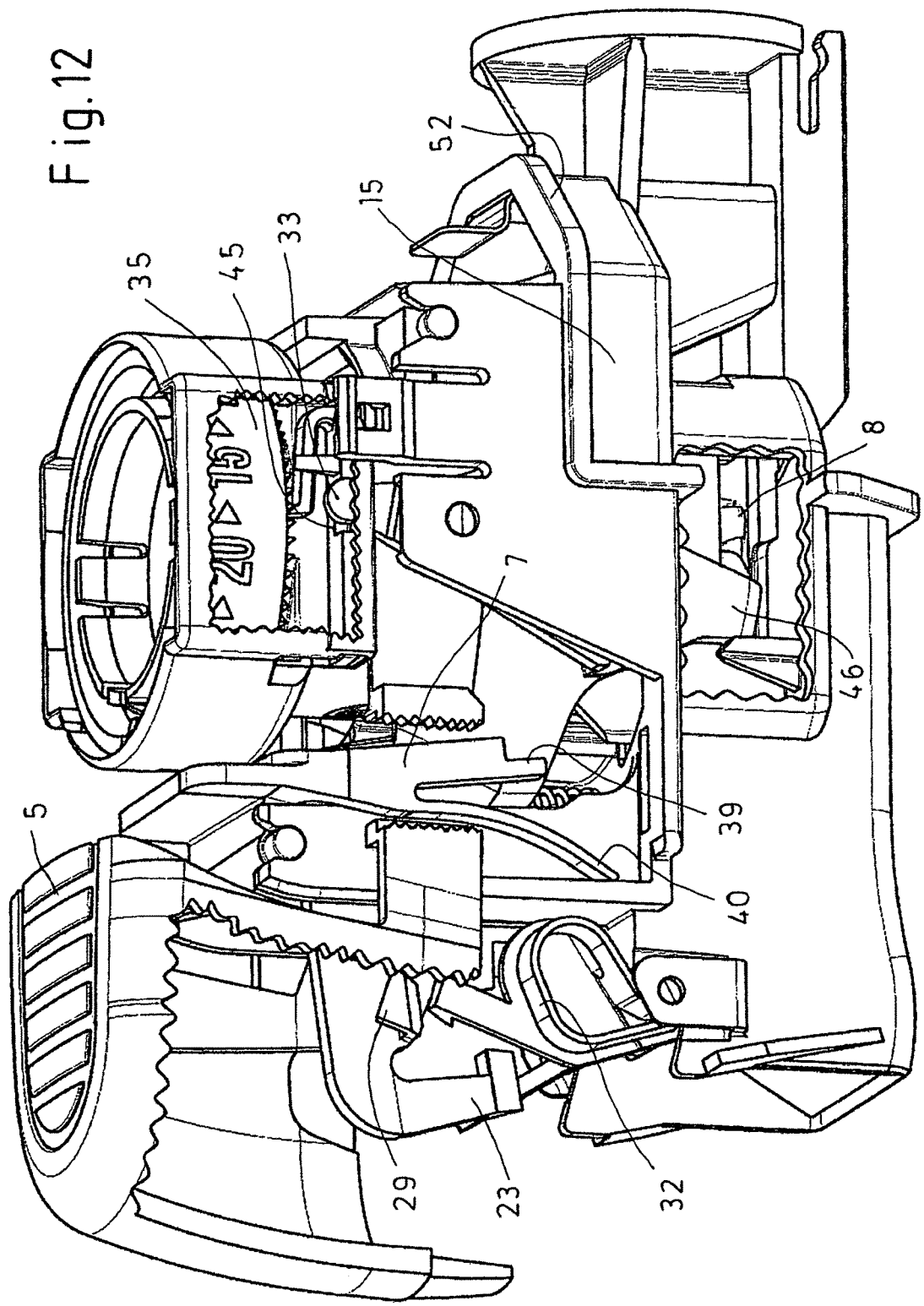

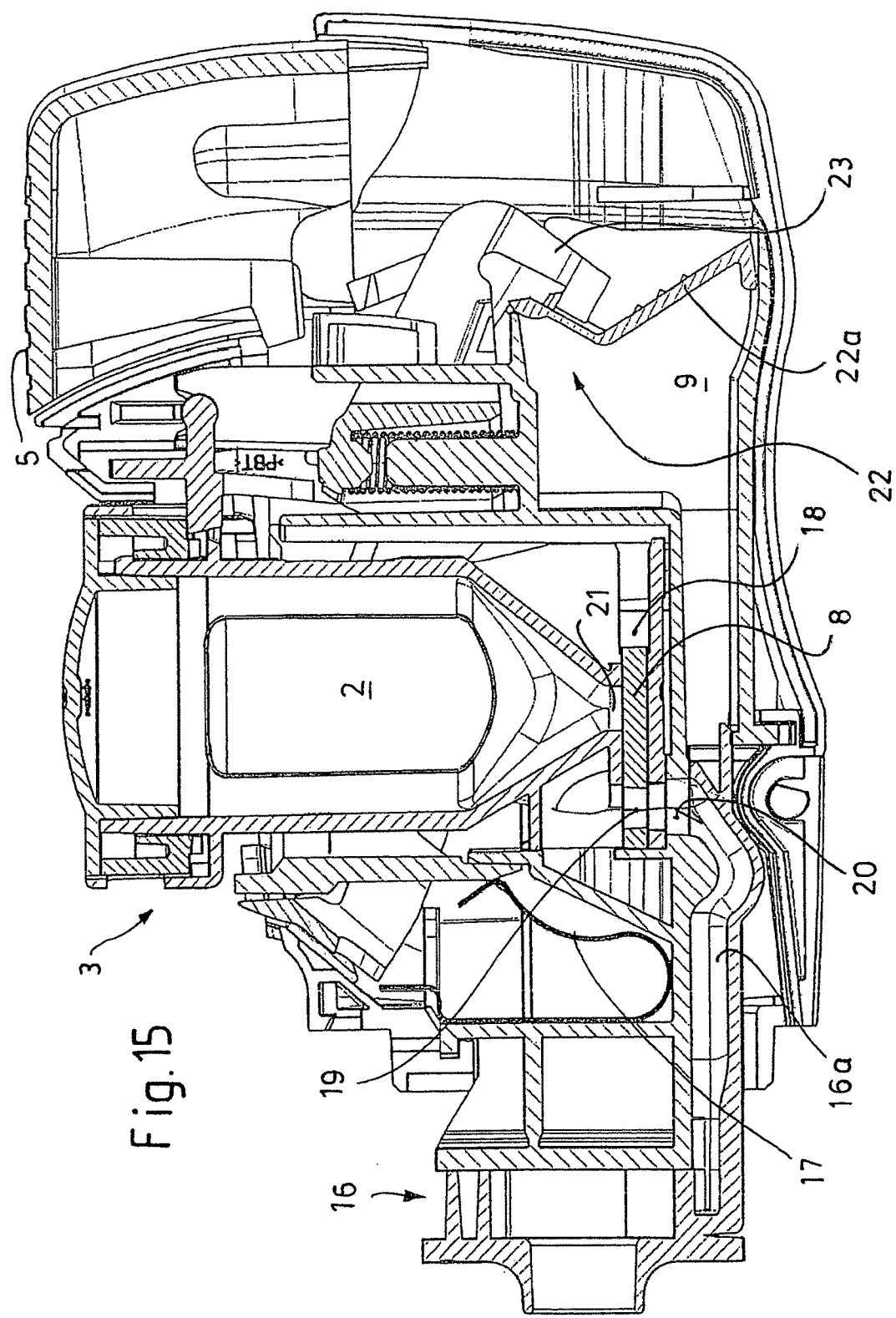

INHALATION DEVICE FOR POWDERED DRUGS

The invention refers to an inhalation device for powdered drugs to be received by a patient by an inhalation-caused air stream, comprising at least one powder reservoir, metering means for repeatedly metering a powder dose from the reservoir, a transportation mechanism for moving said metering means from a filling position for receiving a powder dose into an emptying position for releasing said powder dose into a powder channel, and at least one activating device for manual operation by the patient, said activating device being operatively connected to said transportation mechanism such that upon operation a single powder dose is being metered, said activating device comprising a dosage key acting on said transportation mechanism when pressed by the patient and further comprising an advancing mechanism for advancing a counter means each time the inhalation device has been activated by the patient so that a powder dose has been released into the powder channel, wherein the counter means comprises a mechanical index coupled to a locking mechanism blocking the dosage key and/or the activating device and/or the transportation mechanism after a predetermined number of metering cycles after detection of the index, wherein the locking mechanism includes a locking lever for positive engagement with the dosage key and/or the activating device and/or the transportation mechanism in the blocked condition.

A powder inhaler of above-referred kind is for instance disclosed in EP 1 616 592 B9.

In the field of treating bronchial diseases but also other diseases in which medication can be affected by way of the respiratory tract, it is generally known to apply medicaments in powder form. Of course, in the art are also known devices for atomization of solutions of suspensions to provide inhalable aerosols.

The present invention relates to an inhaler for the administration of powdered pharmaceuticals in form of a multi-dose dry powder inhaler, preferably with a dosing counting or indexing means provided in the inhaler or on a cartridge for powdered pharmaceuticals.

As aforementioned, an inhaler of this kind is disclosed in EP 1 616 592 B9. This reference refers to an inhaler for providing a large number of doses of a pharmaceutical powder medicament from a single reservoir space which medicament can be received by the patient by means of an air stream which has to be induced by suction to a mouthpiece by the patient.

For multi-dose inhalers an important design aspect is the metering accuracy of the device.

Another important design aspect of inhalation devices of the above-referred kind are the use properties of the device.

The inhalation device has to be designed such that the user clearly may make out whether the device is ready for inhalation, and whether the device has a certain and sufficient residual amount of powder doses. Moreover, the device has to be sufficient fail-safe and safe against operating errors of the user. For instance double dosing has to be prevented in any event by an appropriate design of the metering technique.

In particular, EP 1 616 592 B9 refers to a locking mechanism, locking an activating device and/or transportation mechanism of the inhaler after a predetermined number of metering cycles.

This known inhalation device comprises an activating device for manual engagement by the patient for repeatedly metering a dose of medicament to be administered to the patient, an advancing mechanism for advancing a counting or indexing means each time the activating device has been engaged by the patient so that a dose of medicament has been released for administration to the patient, the counting or indexing means comprises an index, the index being detectable by a detection means of the inhaler, and the detection means being coupled to a locking mechanism, the locking mechanism blocking the activating device and/or any transportation mechanism of the inhaler delayed by a pre-determined number of metering cycles since detection of the index. The activating device is arrested in a position different from the operating position indicating the blocking state of the inhaler. This arrangement allows to block further use of the inhaler after removal of a number of doses from the reservoir space or an approximate number of doses left in the reservoir space with a simple, inexpensive and reliable mechanism so that an improved security of the patient using the inhaler can be obtained. In this manner, a patient is prevented from trying to dose from an empty reservoir space causing an inappropriate lack of required medicine. Insofar, the known inhalation device provides an enhanced usability.

The advancing mechanism of the inhaler according to EP 1 616 592 B9 comprises a signaling lever for biased engagement with a notch in the counter or indexing means. The signaling lever in turn is in hinged connection with a rest lever such that a movement of the signaling lever upon detection of the index, i.e. a notch in the counter ring, is transmitted to the rest lever. The rest lever comprises a pilot section allowing the rest lever being biased against the activating device and/or the transportation mechanism after the transportation mechanism reaches the emptying position for releasing a dose of medicament powder and thus arresting the activating device and/or the transportation mechanisms so that no further dosing cycle can be performed. In that blocked state of the inhaler, the dosage key assumes a position half way between its initial starting position and its fully depressed position.

Although such blocking mechanism turned out to be very reliable, the production of such inhalation device due to the number of moving parts is quite expensive and complicated.

Moreover, the counter means of the known inhaler is rotated by a gear drive which due to the required gear reduction is also very complicated to produce.

Yet another concept of a blocking mechanism is for instance disclosed in WO 2008/077623 A1. This lockout system blocks the path of a closure cap after a predetermined number of metering cycles. The locking device is disclosed in this reference blocks the closure cap of the inhaler in such a way that the closure cap is no longer moveable into the closure position. The blocking mechanism itself includes a locking stirrup which comprises two limbs connected by a joke. The joke of the locking stirrup is pressed against a drum counter by a spring. The drum counter includes three counter wheels, each counter wheel being provided with a groove. Once the grooves are in line in a specific counter state, locking stirrup may be displaced such that the ends of the limbs engage into the path of movement of entrainment portions of the closure cap. This mechanism is particularly adapted for use with a drum counter and requires also several moveable parts as well as at least one spring element in order to ensure a reliable operation.

Another type of inhaler for discharging liquid agent into an air stream is for instance disclosed in US 2010/0083963 A1.

It is accordingly an object of the present invention to provide an inhalation device of the above-referred kind which has a simplified design. These and other objects are achieved by an inhalation device according to independent claims 1 and 12.

According to one aspect of the invention, there is provided an inhalation device for powdered drugs to be received by a patient by an inhalation-induced air stream, comprising at least a powder reservoir, metering means for repeatedly metering a powder dose from the reservoir, a transportation mechanism for moving said metering means from a filling position for receiving a powder dose into an emptying position for releasing said powder dose into an emptying position for releasing said powder dose into a powder channel, and at least one activating device for manual operation by the patient, said activating device being operatively connected to said transportation mechanism such that upon operation a single powder dose is being metered, said activating device comprising a dosage key acting on said transportation mechanism when pressed by the patient, and further comprising an advancing mechanism for advancing a counter means each time the inhalation device has been activated by the patient so that a powder dose has been released into the powder channel, wherein the counter means comprises a mechanical index coupled to a locking mechanism blocking the dosage key and/or the activating device and/or the transportation mechanism after a predetermined number of metering cycles after detection of the index, wherein the locking mechanism includes a locking lever for positive engagement with the dosage key and/or the activating device and/or the transportation mechanism in the blocked condition, the inhalation device being characterized in that the locking lever includes signaling means integrally formed therewith and engaging the index after said predetermined number of metering cycles.

"Signaling means" in the sense of the present invention is a contour or profile which comes into positively locking engagement with a mechanical index of a counter means and thereby triggers the locking mechanism. According to the instant inventive concept, such signaling means comprises a contour, cam surface, notch or pin integrally formed with said locking lever and positively engaging said index after said predetermined number of metering cycles so as to for example allow a pivot or translatory movement of said locking lever from an idle position into a blocking position.

That the inhalation device is activated in the sense of the instant application means that a powder dose has been released into said powder channel so that the device is ready for inhalation. In that condition of the inhalation device, the patient may inhale one powder dose by applying suction to a mouthpiece, thereby triggering an automatic return movement of the metering means so that the device is reset and the patient may start another metering cycle.

Thus, according to the inventive concept, no additional rest lever being biased against the activating device is required. Thus, the number of moveable parts is reduced remarkably.

Reduction of the number of moveable parts is not only an advantage from the production perspective but also enhances the accuracy of dosage count until the lockout position is reached, i.e. until the predetermined number of metering cycles has been completed.

One advantageous embodiment of the inhalation device according to the present invention is characterized in that the mechanical index is formed by a notch or cam engaging the locking lever after said predetermined number of metering cycles so as to allow a pivot movement of the locking lever such that the locking lever comes into positive engagement with the dosage key and/or the activating device and/or the transportation mechanism.

The locking lever may for instance be designed as an injection-molded part from thermoplastic material.

The locking lever may comprise a tongue member or a projection engaging an index of the counter ring.

Preferably, the locking lever comprises an integrally formed spring leg biasing the locking lever into engagement with the index. The index for instance may be a notch in the counter ring of the inhalation device. For example, if the locking lever engages a notch at a predetermined location on the counter ring, the locking lever by the resilience of its integrally molded spring leg is caused to fulfill a pivot movement into its blocking position.

One preferred embodiment of the inhalation device according to the present invention is characterized in that the spring leg of the locking lever is only loaded/biased while the dosage key is being pressed by the patient.

Such design has the advantage that the spring leg is not biased/loaded all the time, but only when the inhaler is being operated by the patient. As a result, eventual fatigue of the spring leg is prevented.

In a particular preferred embodiment of the inhalation device according to the invention, the dosage key comprises an actuation means, in particular an actuation rib acting on the spring leg while being pressed.

In one advantageous embodiment of the inhalation device according to the invention, the locking lever positively engages the dosage key in the blocked condition of the inhalation device.

In that blocked condition of the inhaler, the dosage key may be arrested in a depressed state, i.e. such that the dosage key remains pressed, thereby unambiguously indicating the blocked state of the device.

The above-mentioned object is also achieved by an inhalation device for powdered drugs to be received by a patient by an inhalation-caused air stream, comprising at least one powder reservoir, metering means for repeatedly metering a powder dose from the reservoir, a transportation mechanism for moving said metering means from a filling position for receiving a powdered dose into an emptying position for releasing said powder dose into a powder channel, at least one activating device for manual operation by the patient, said activating device being operatively connected to said transportation mechanism, such that upon operation a single powder dose is being metered, said activating device comprising a dosage key acting on said transportation mechanism when pressed by the patient, and further comprising an advancing mechanism for advancing a counter means each time the inhalation device has been activated by the patient, so that a powder dose has been released into the powder channel, the inhalation device being characterized in that the advancing mechanism comprises at least one counter slide engaging a counter ring carrying visual information on the number of doses already administered and/or still available, a translatory reciprocal movement of the counter slide causing a stepwise rotary movement of the counter ring.

This new inhalation device is insofar particularly advantageous since it avoids a fairly complicated reduction gear for driving the counter ring, but rather provides a simplified ratchet mechanism.

Another advantage of eliminating a gear train for driving the counter ring is that the accuracy of dosage count is remarkably enhanced.

In a preferred embodiment, the counter slide comprises an integrally formed pawl engaging drive teeth of the counter ring. A reciprocal translatory movement of the counter slide causes a stepwise rotary movement of the counter ring in that the pawl engages the drive teeth of the counter ring.

In a particularly advantageous embodiment, the counter ring defines approximately 60 rotational steps/increments over its circumference, each increment defining one dosage count. Such reduced number of increments additionally provides for maximum dosage count accuracy.

Bidirectional rotation of the counter ring is effectively prevented by a locking ratchet.

These and other aspects and advantages of the inhalation device according to the instant application become readily apparent by the description of preferred embodiments of the inhalation device.

Figure 2:
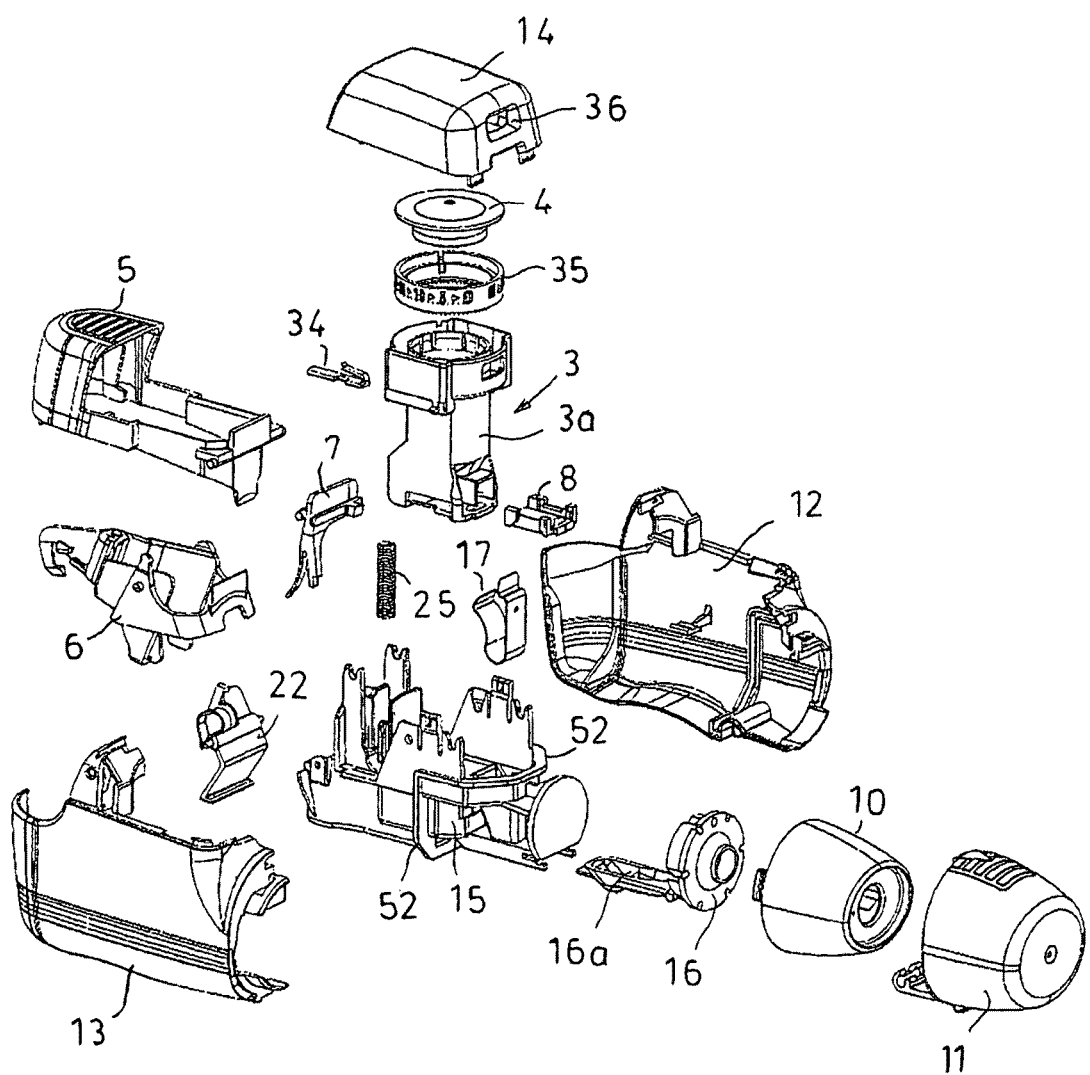
Figure 3:
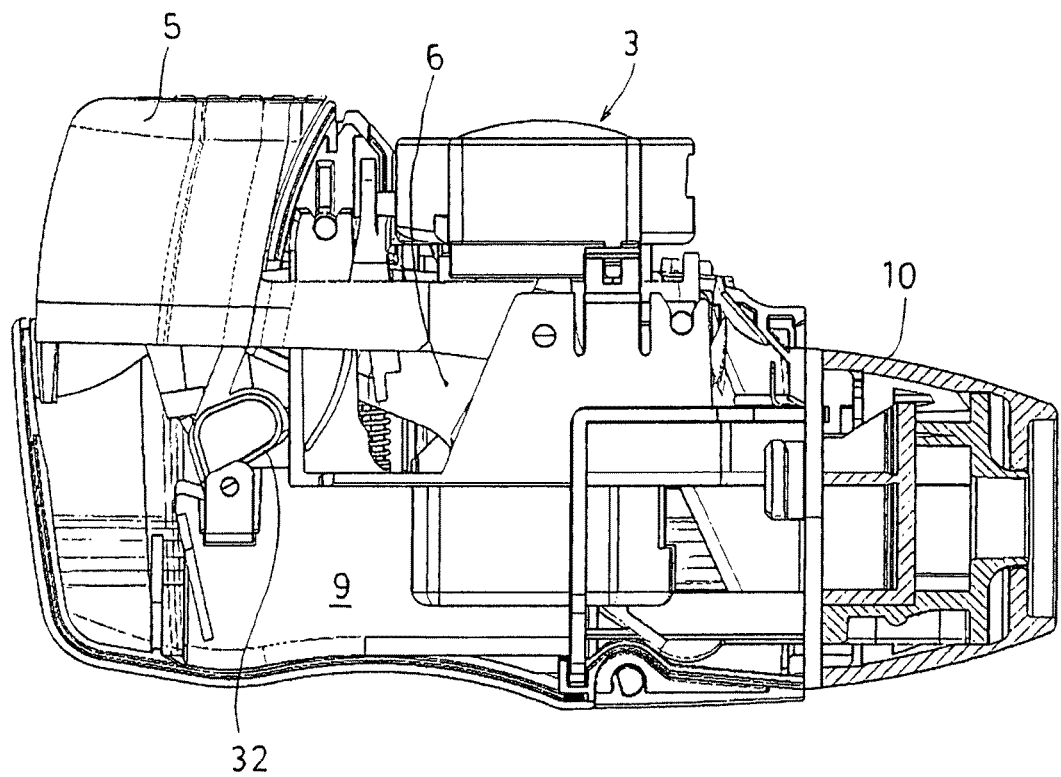
Figure 4:
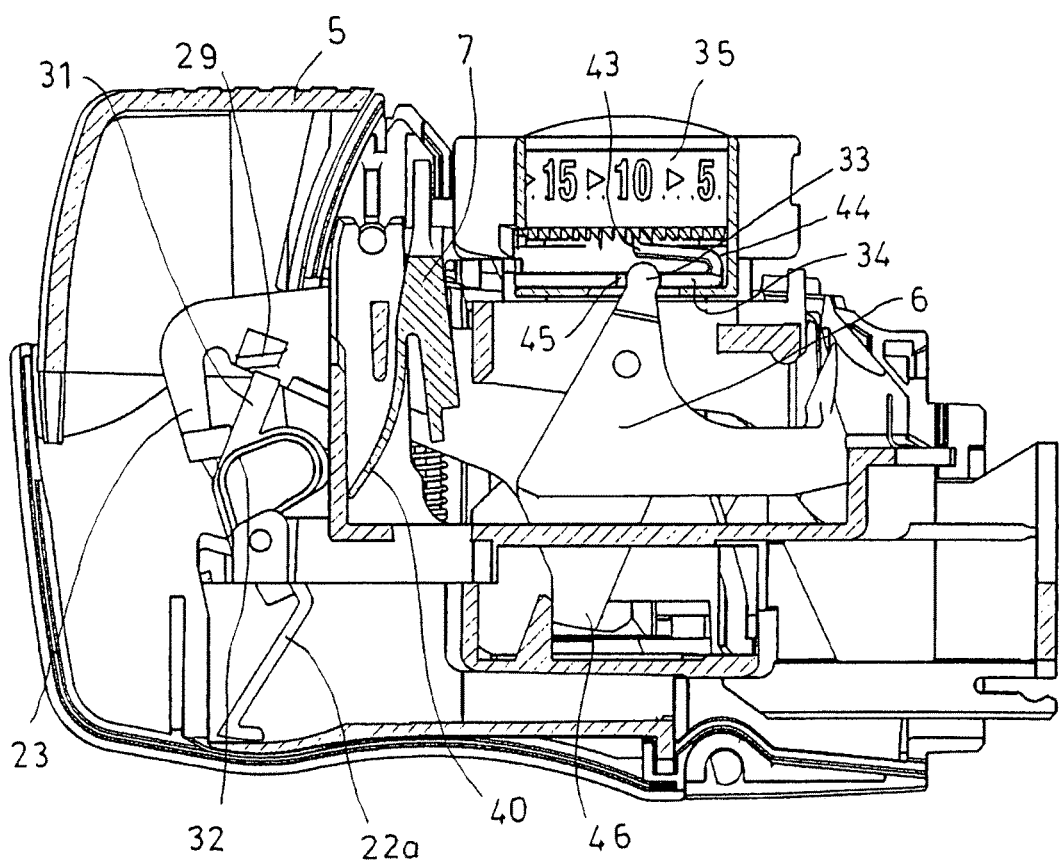
Figure 5:
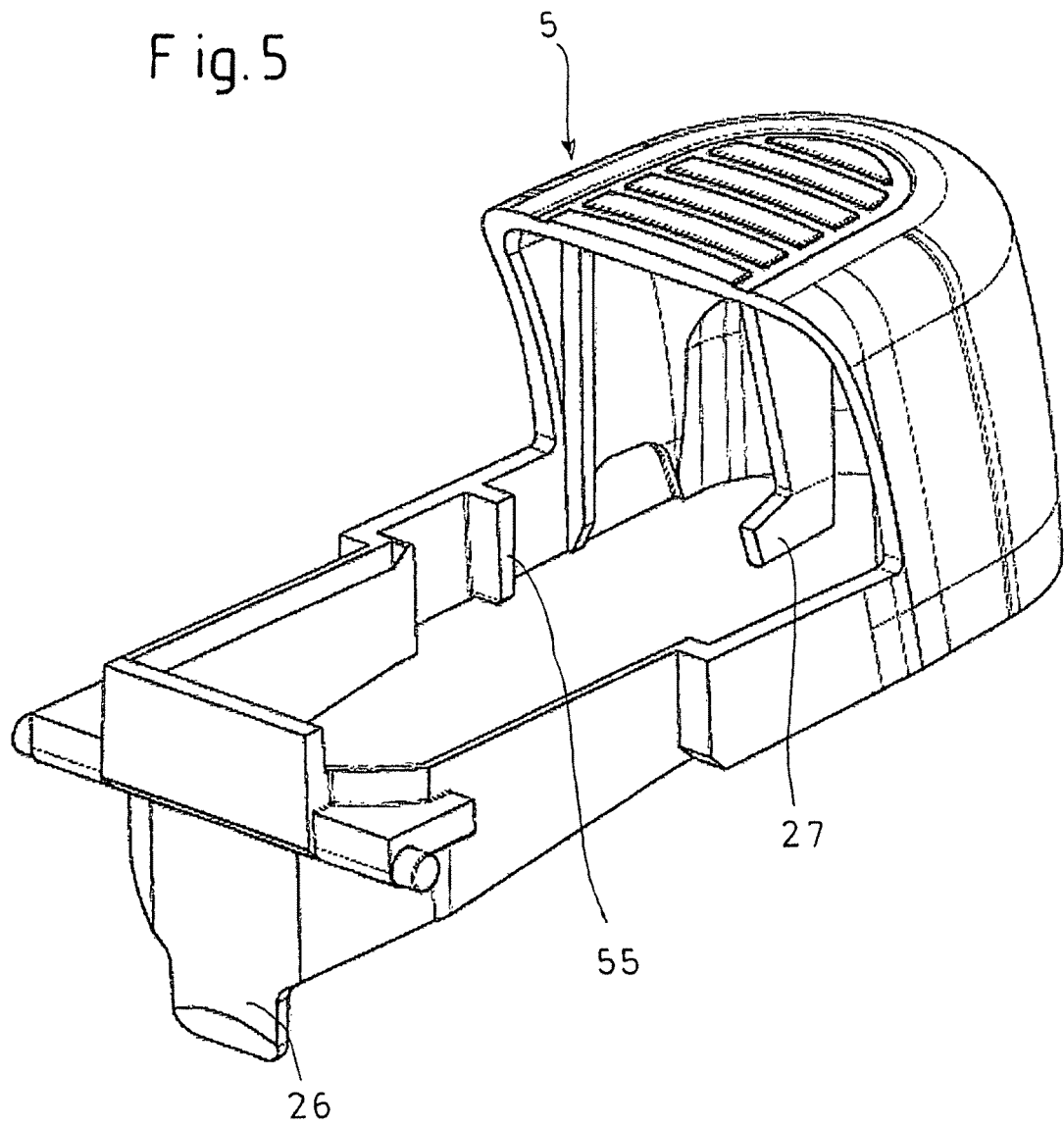
Figure 6:
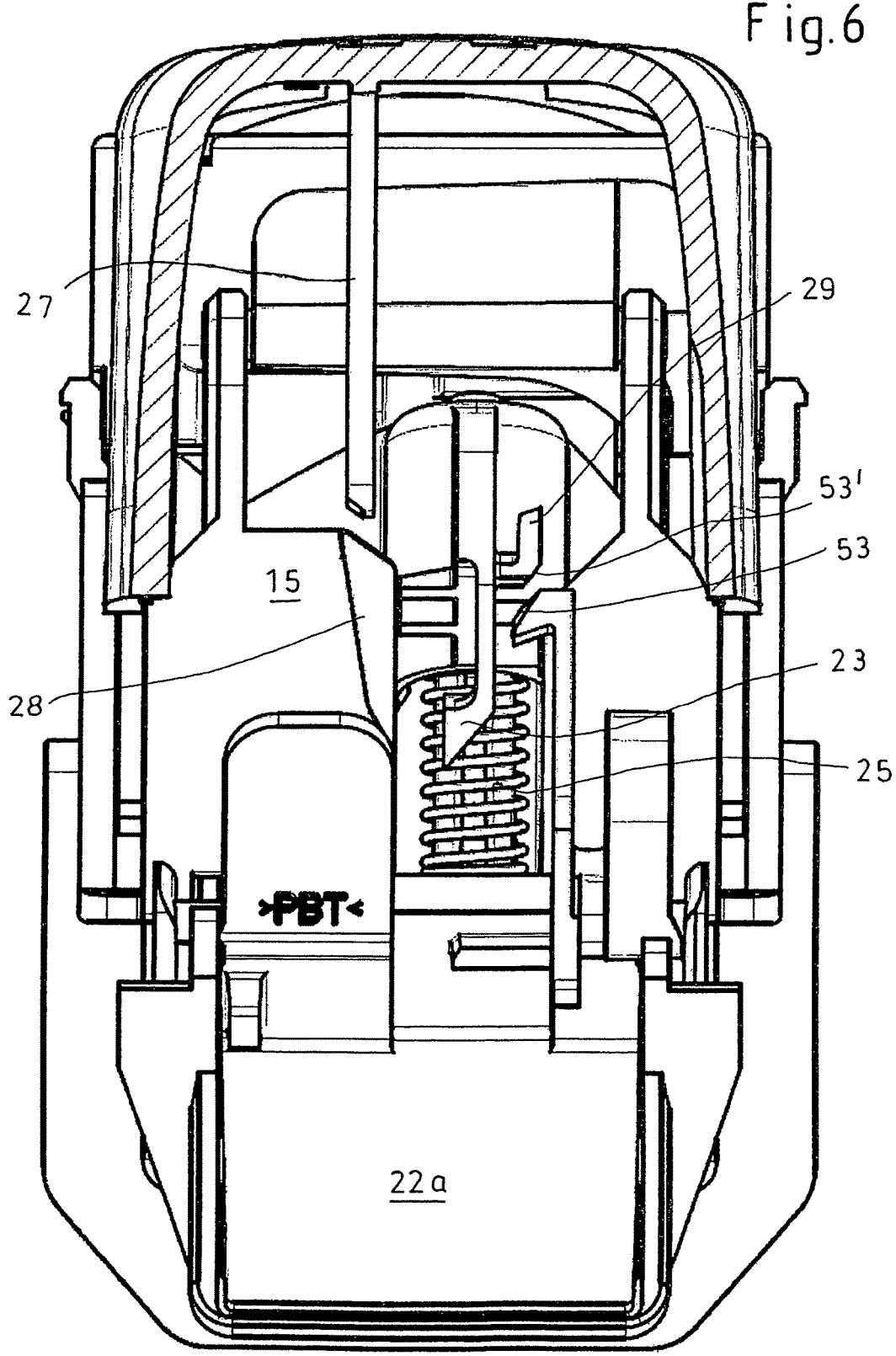
Figure 7A:
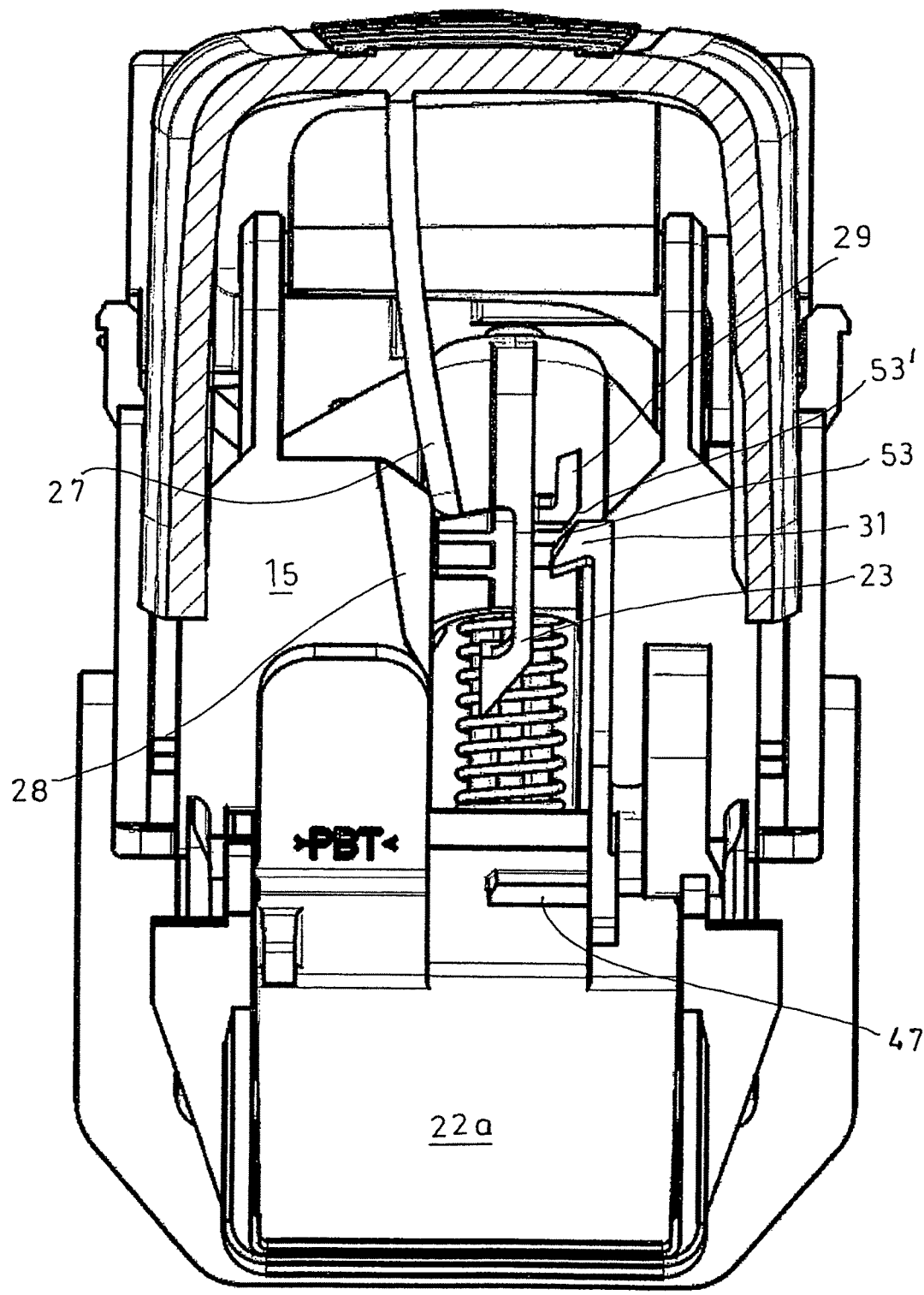
Figure 7B:
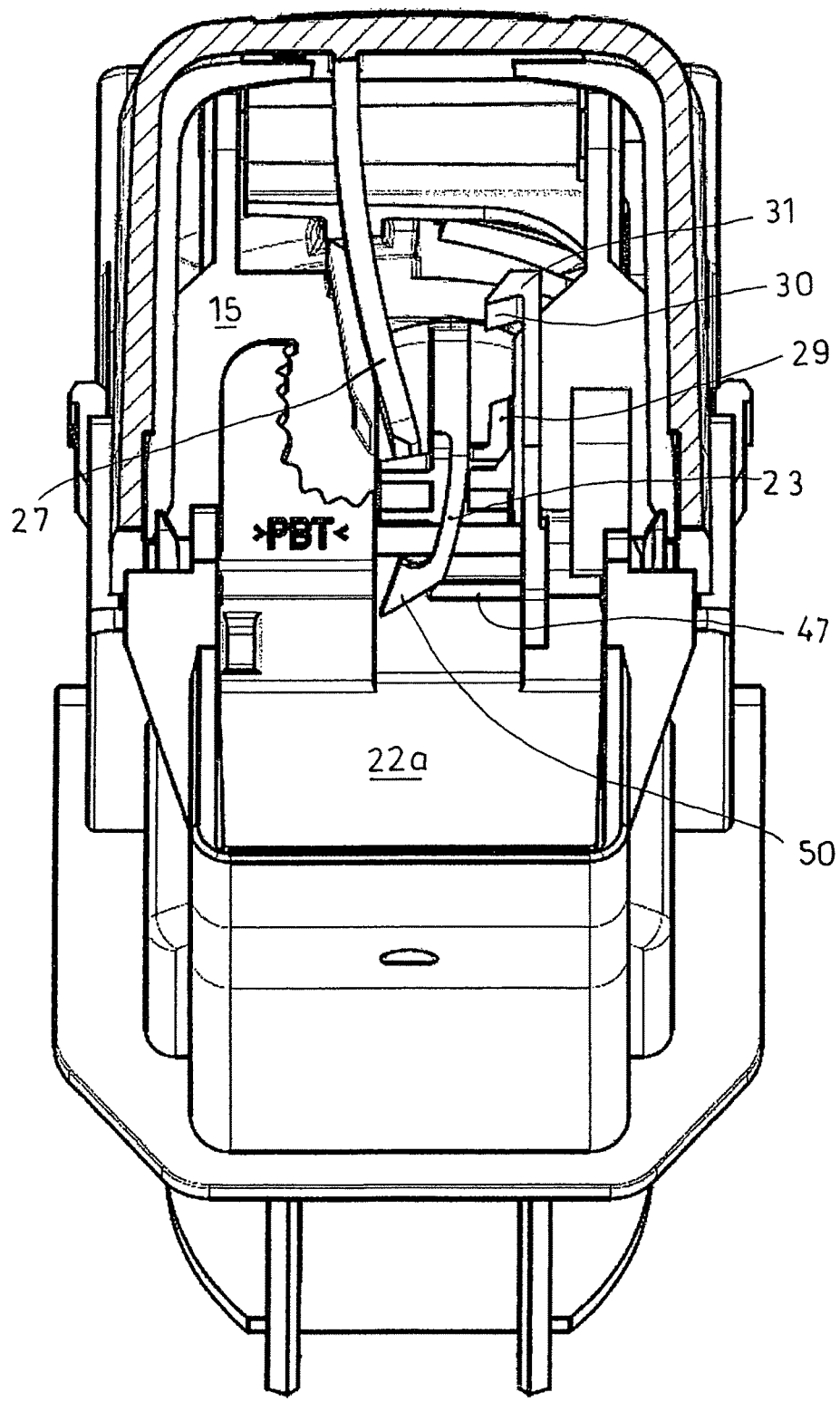
Figure 8A:
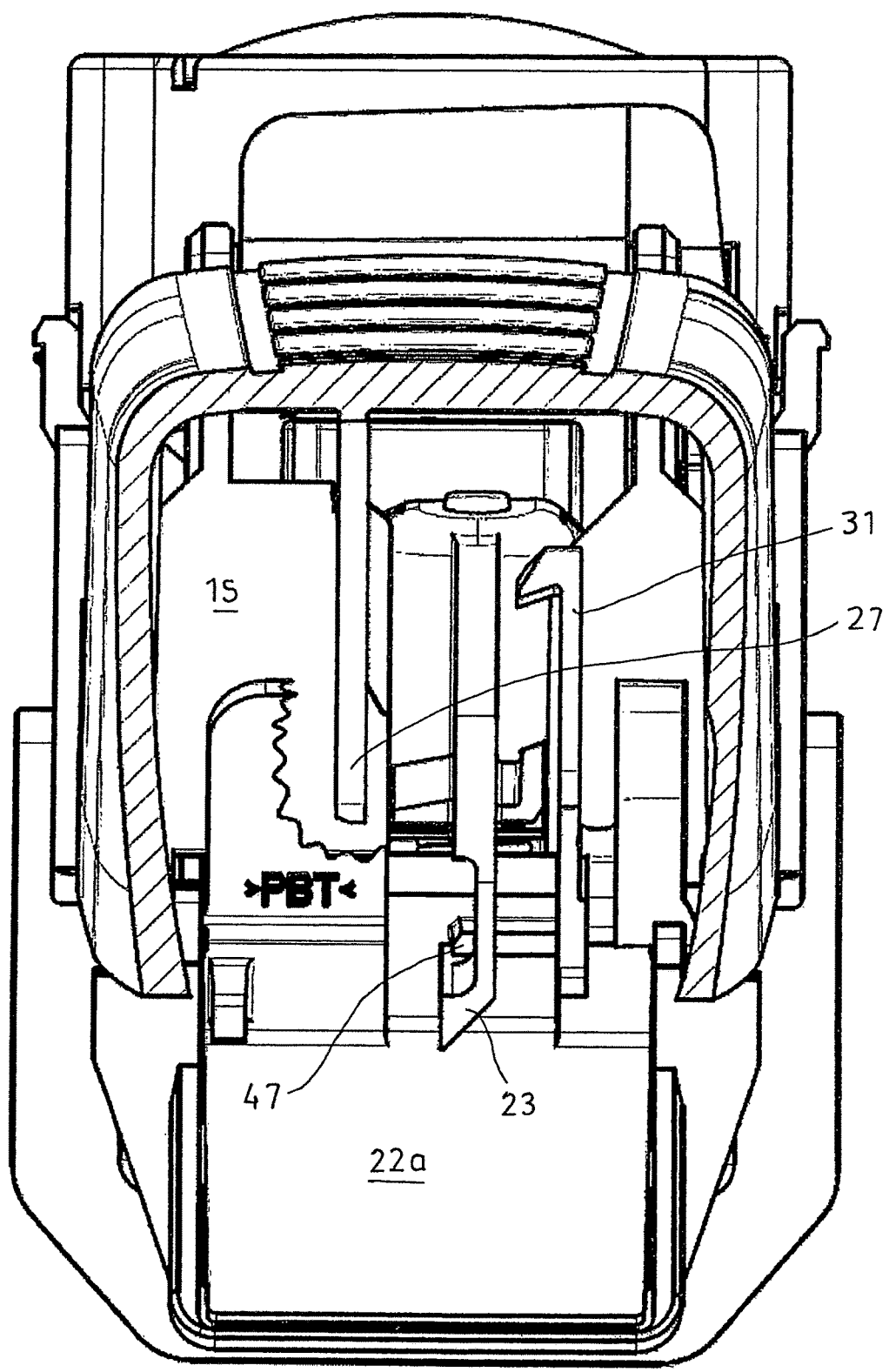
Figure 8B:
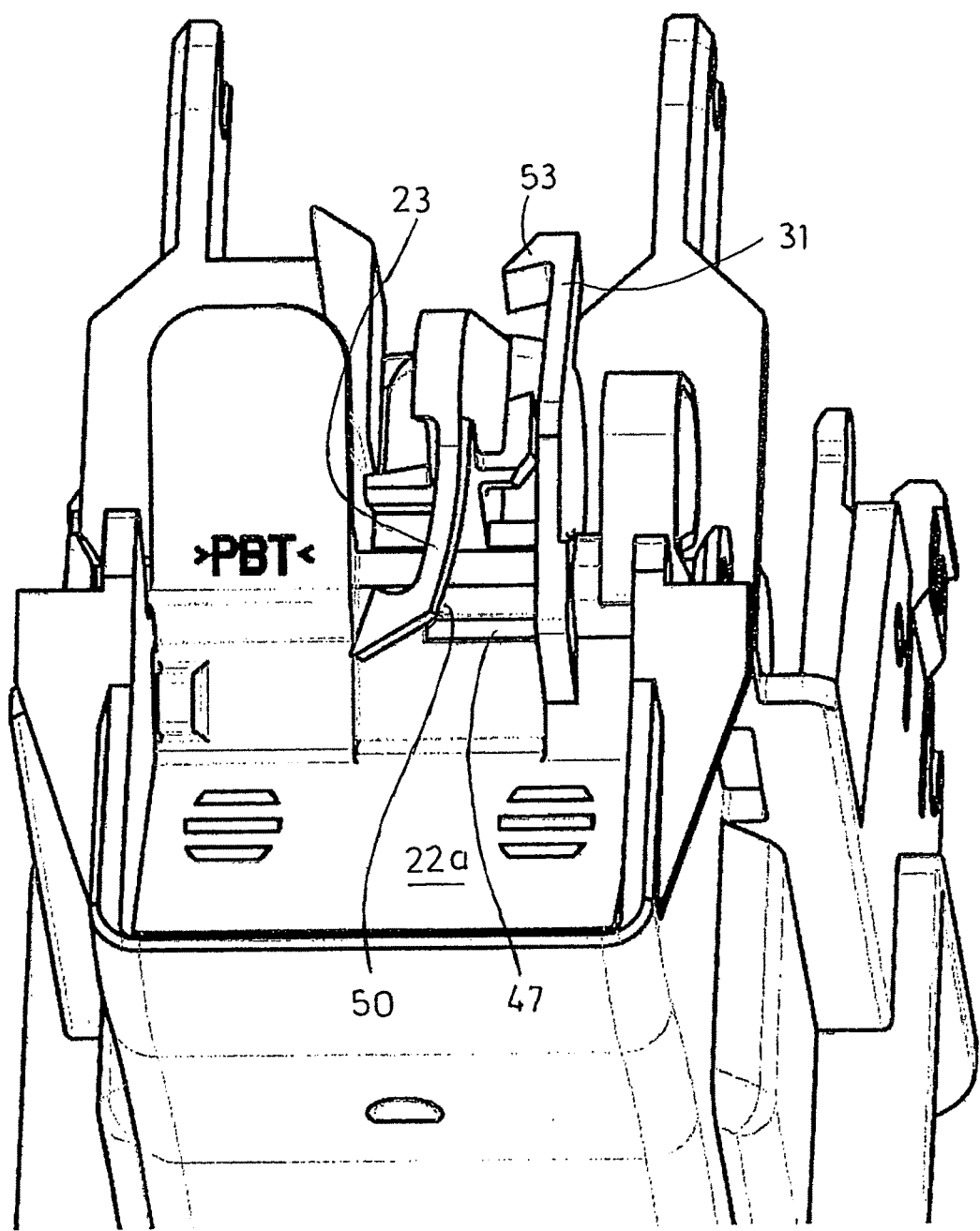
Figure 9:
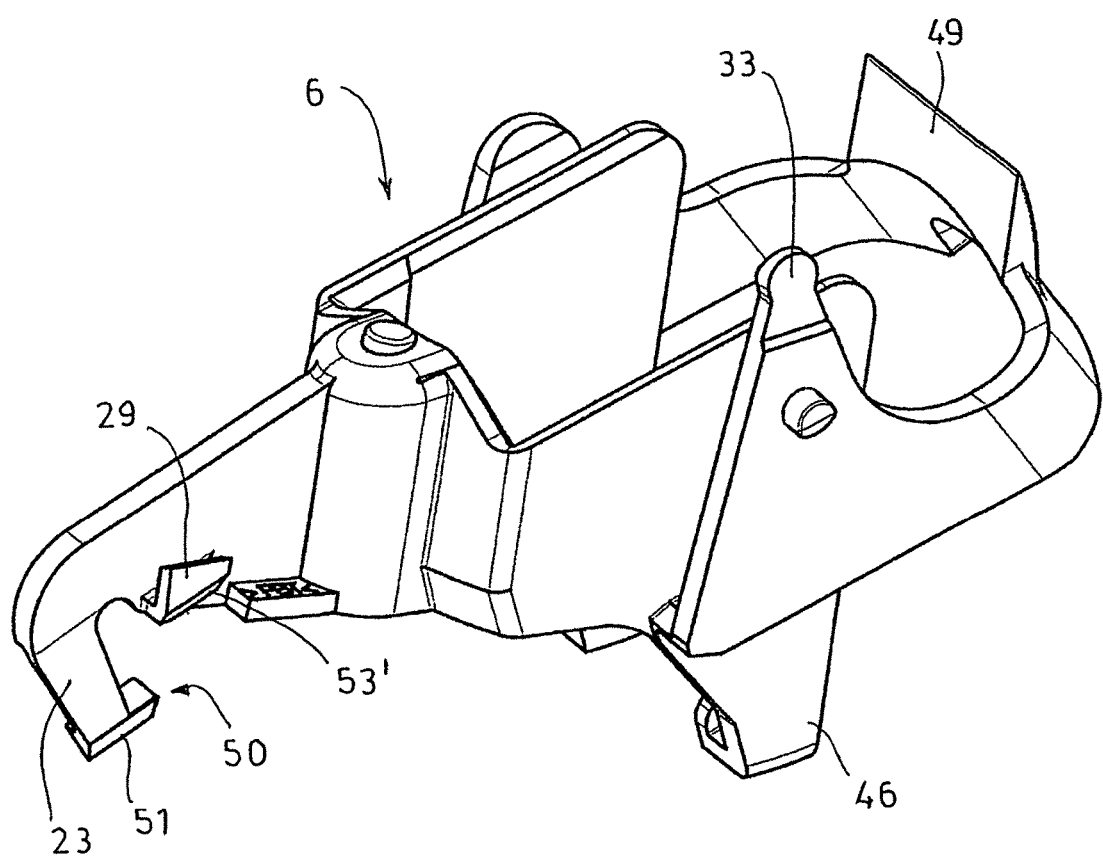
Figure 13:
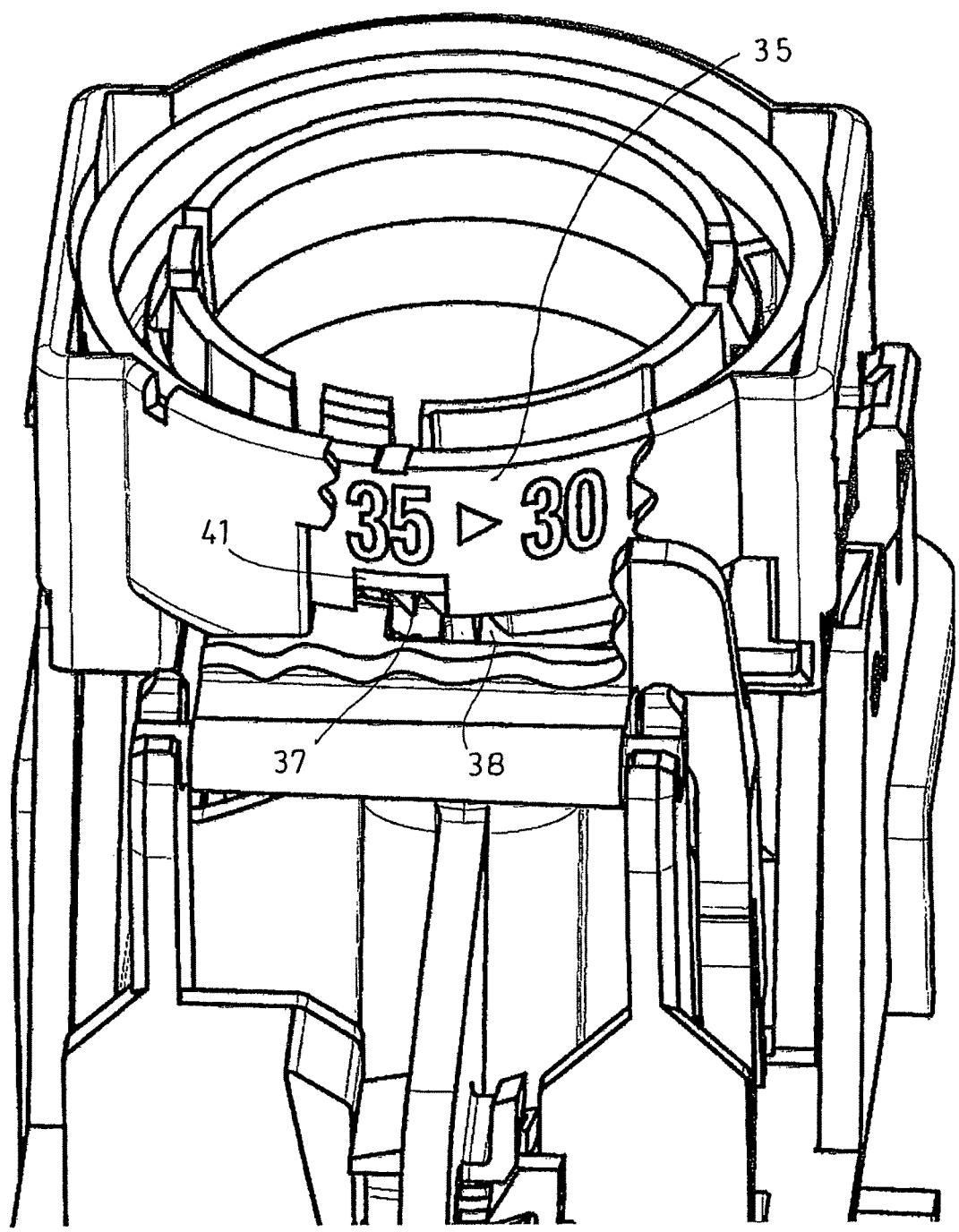
Figure 14A:
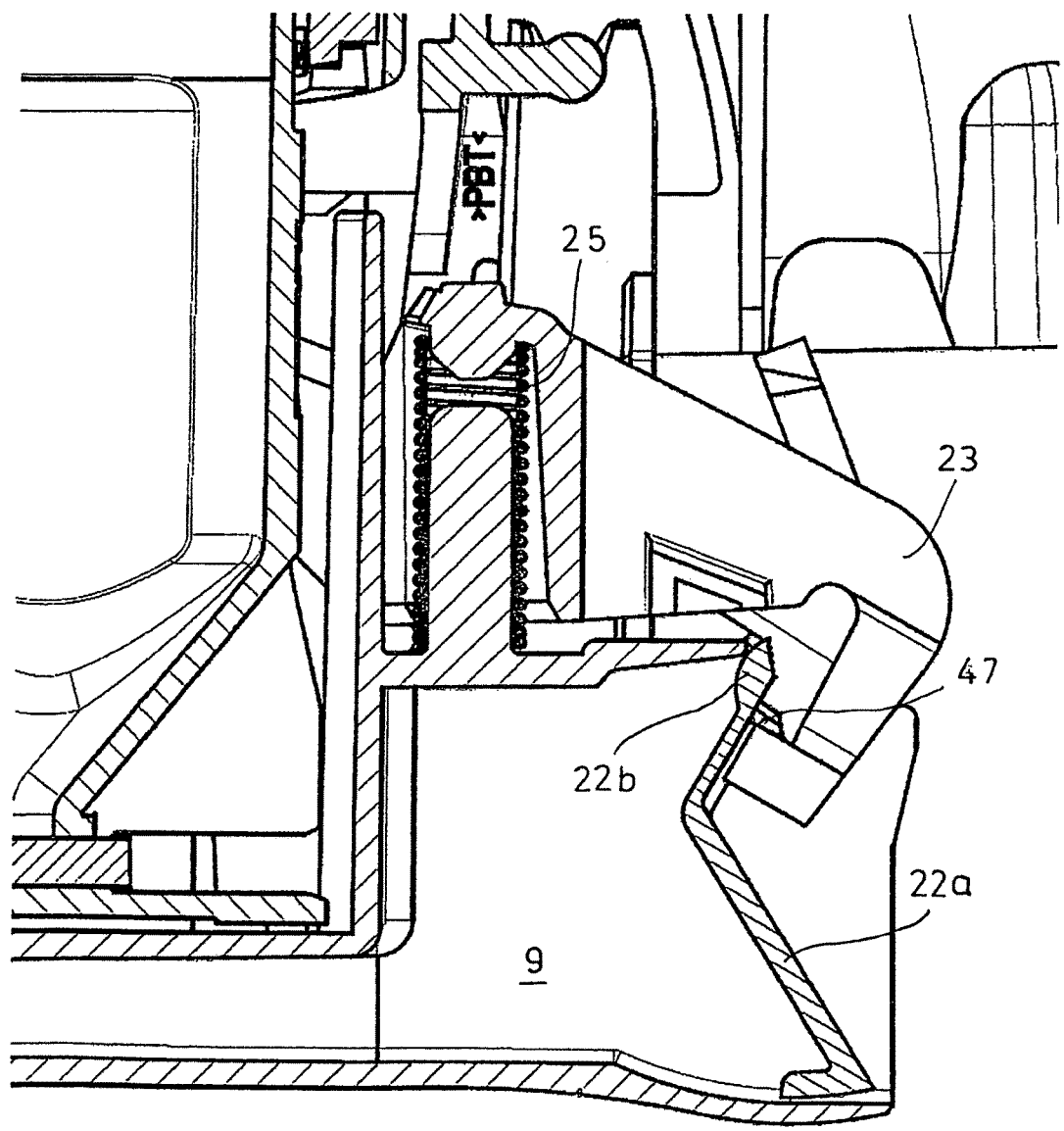
Figure 14B:
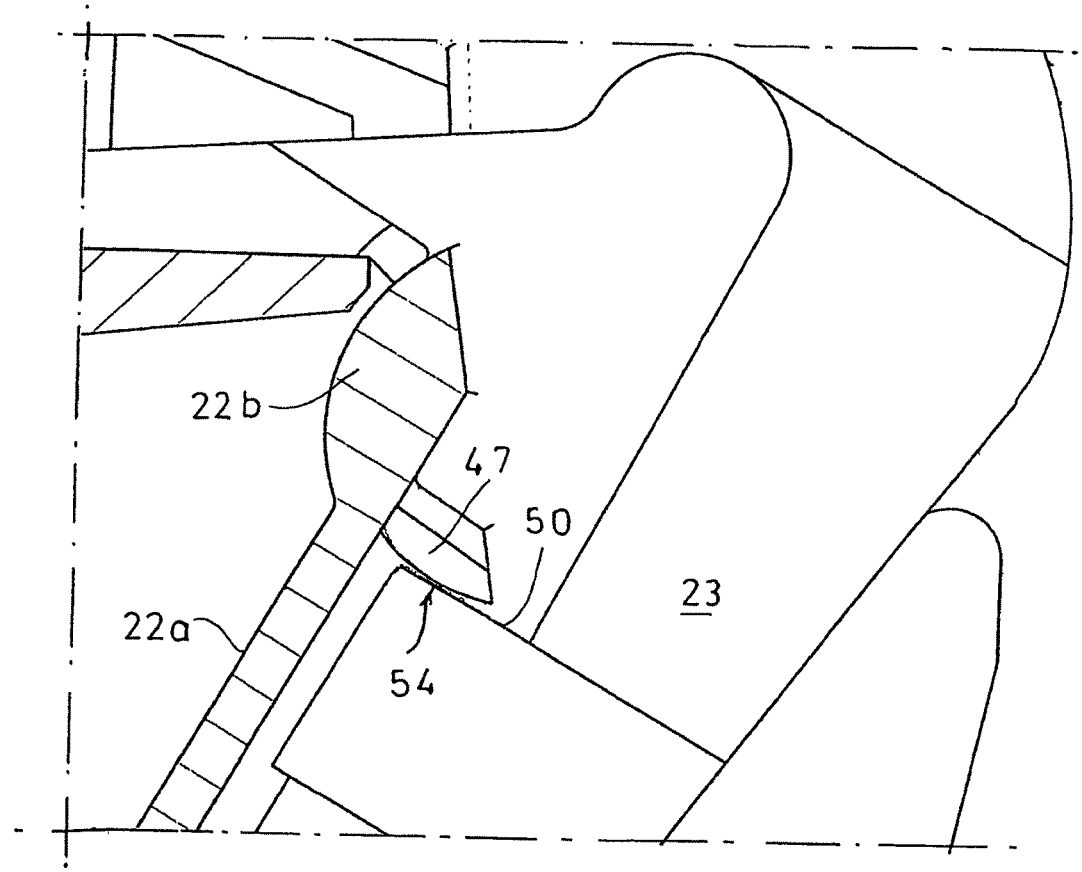
Figure 14C:
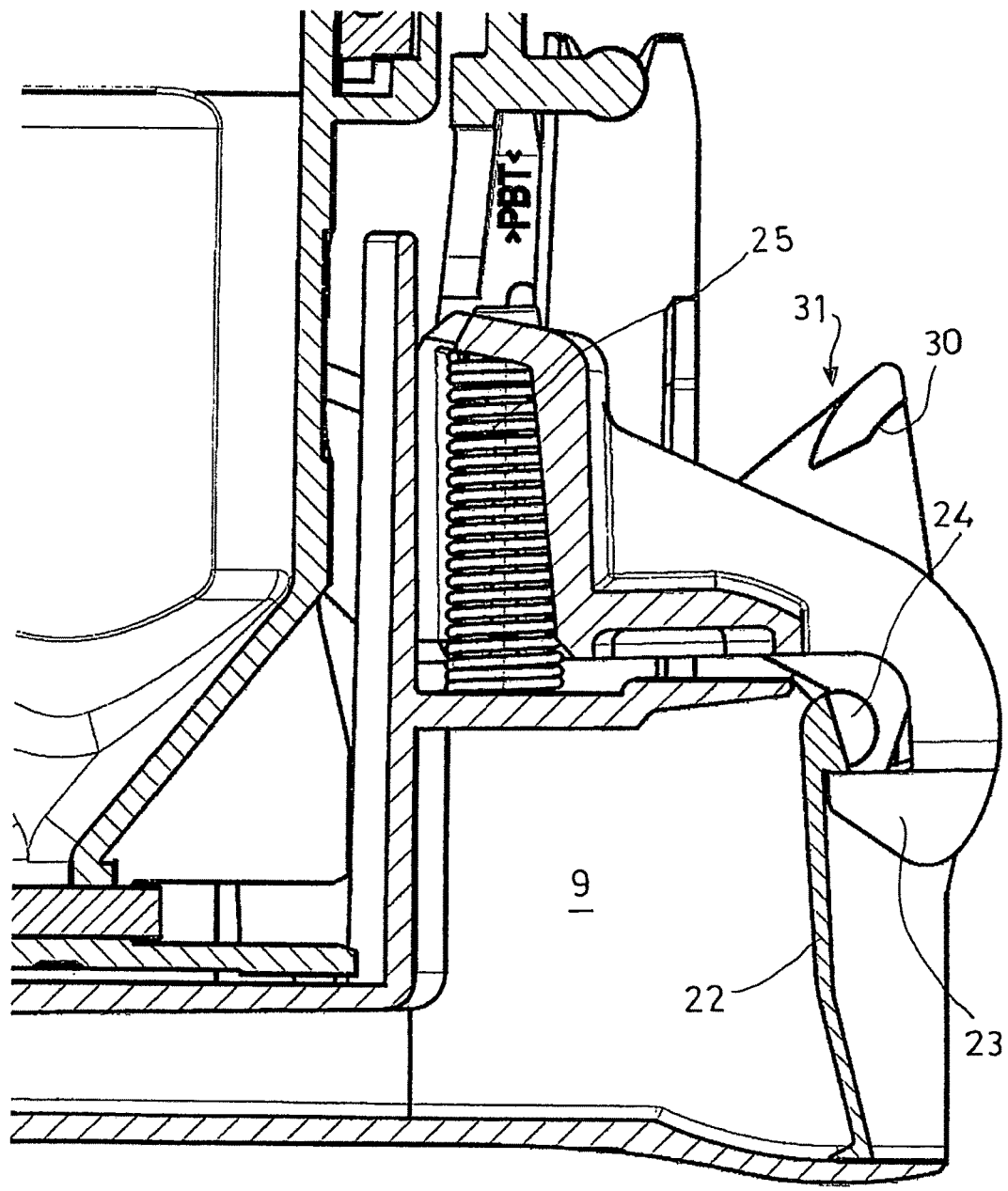
Figure 16:
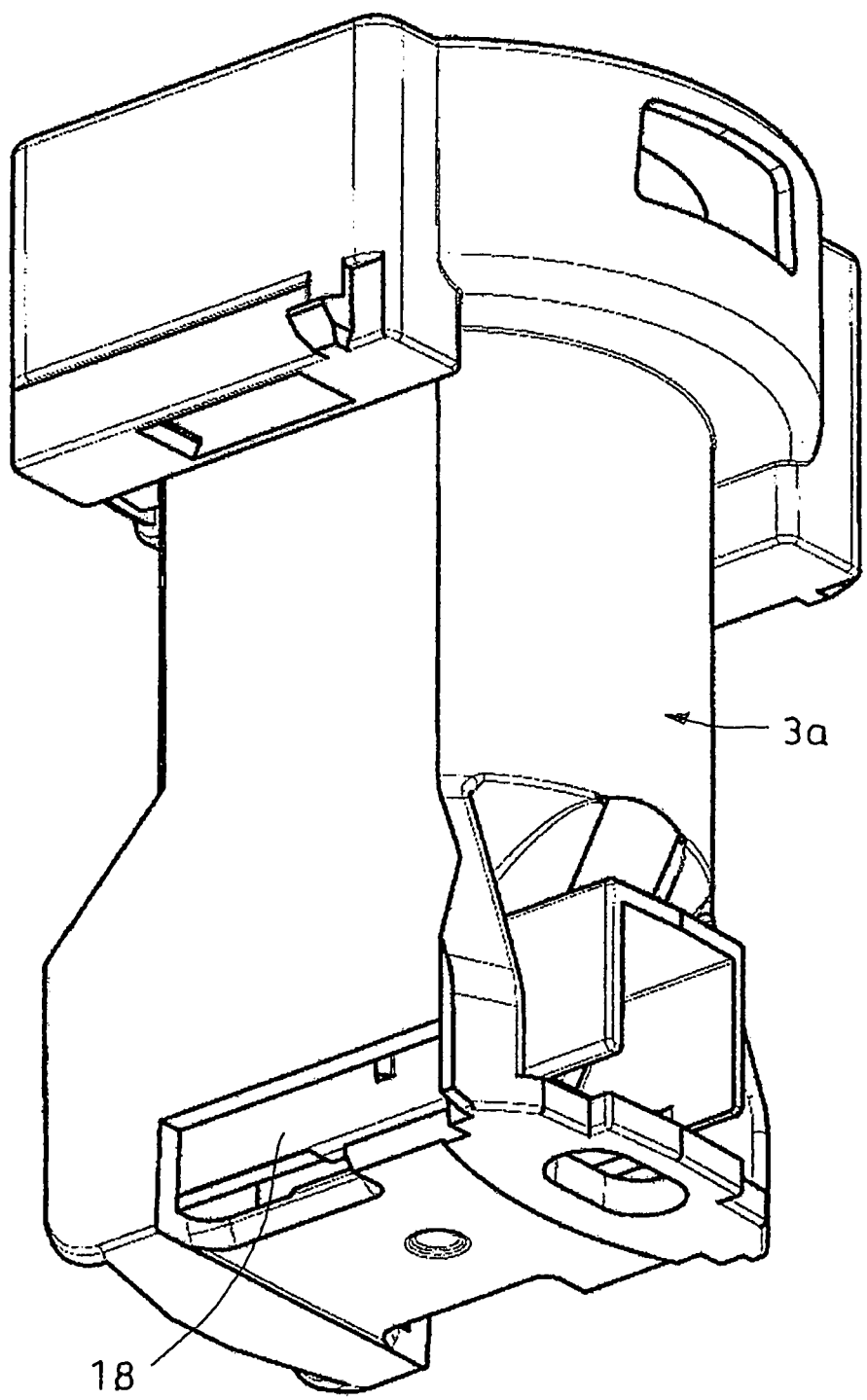
Figure 17:
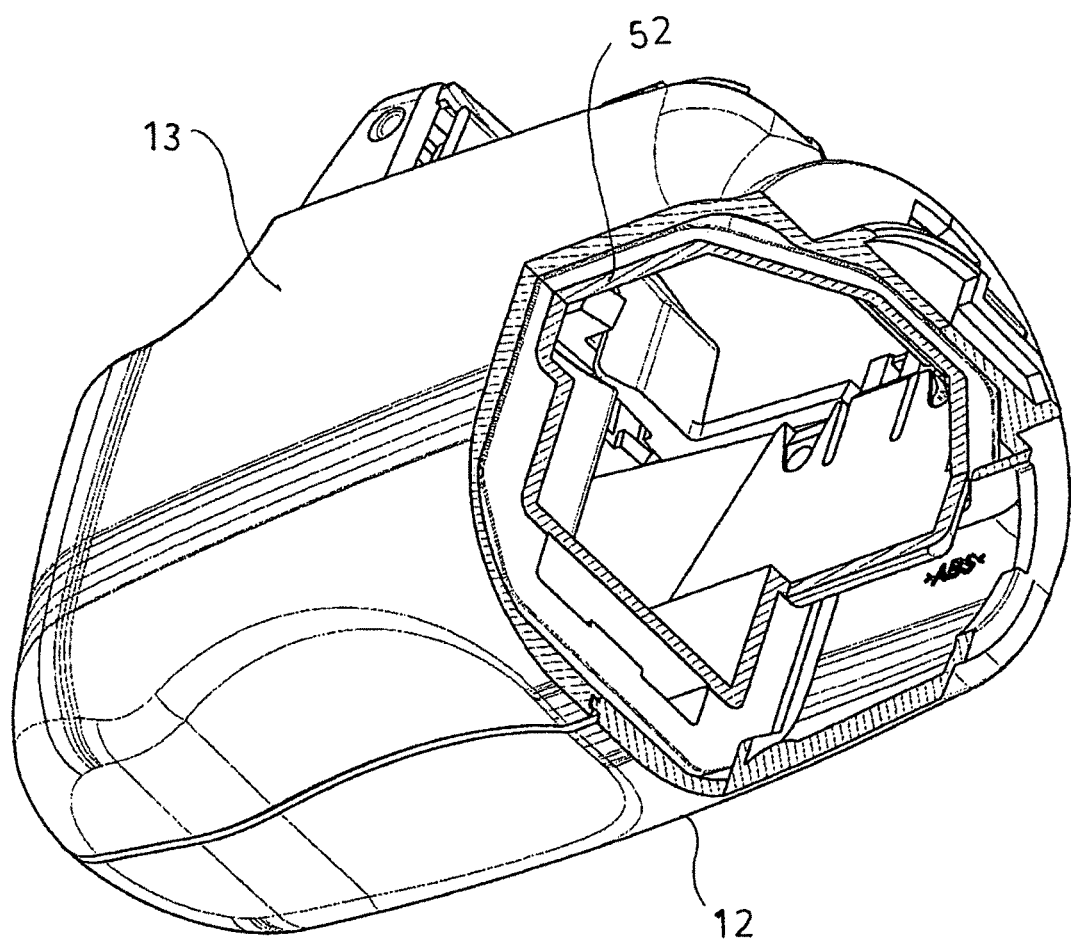
Figure 18:
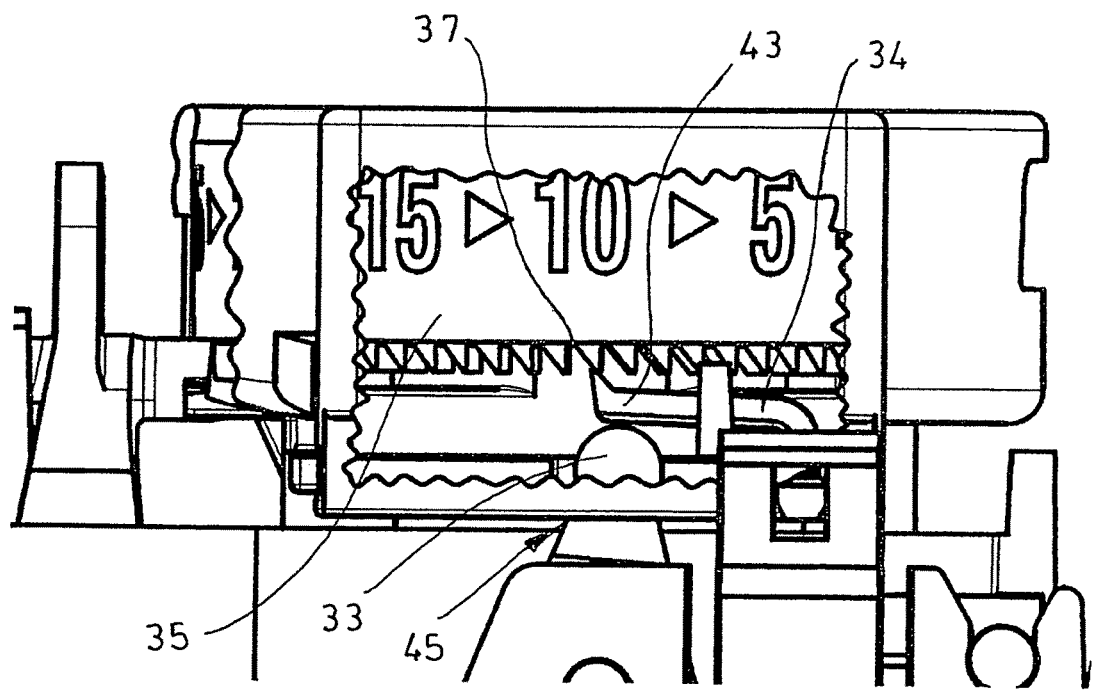
Figure 19:
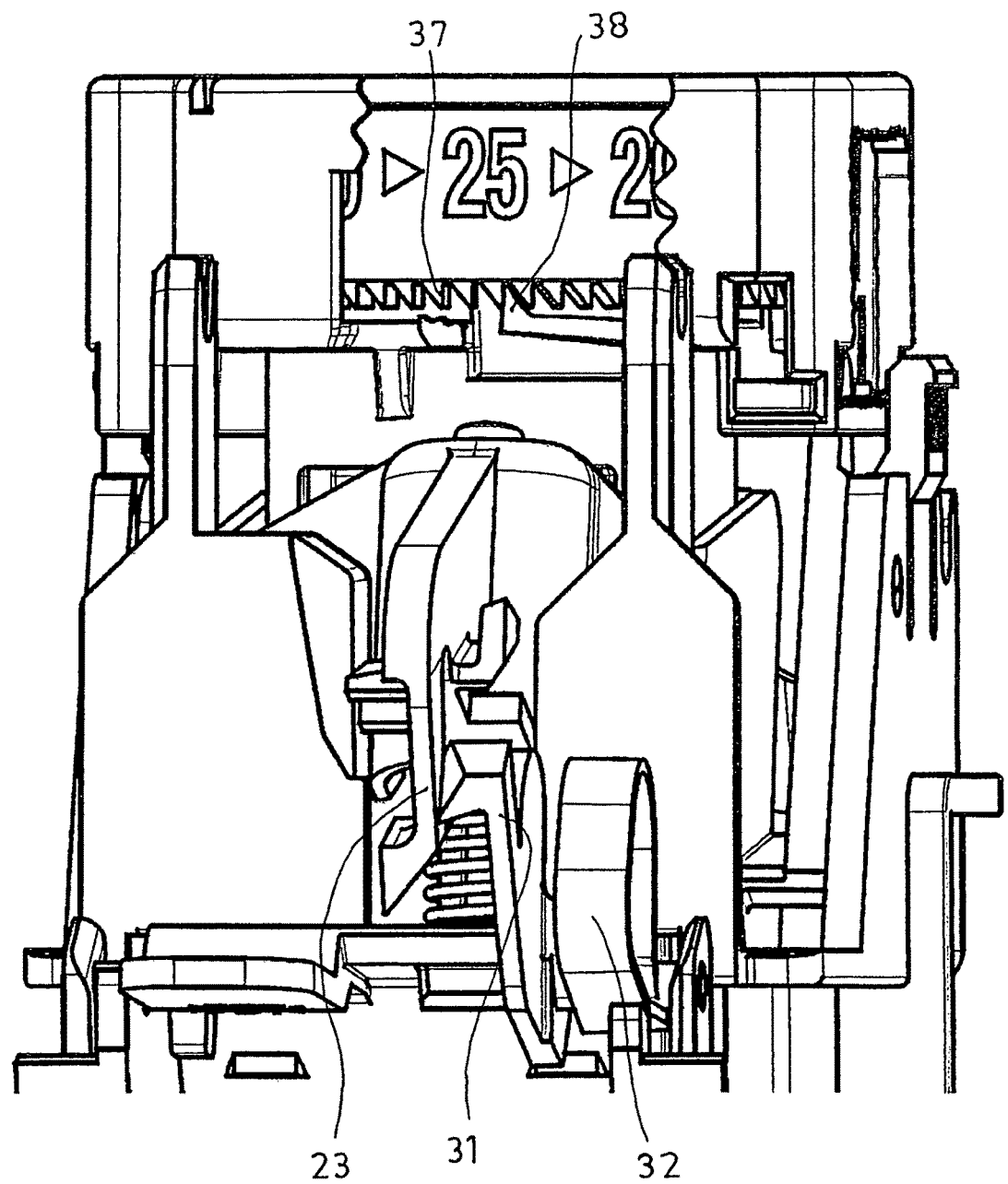
Figure 20:
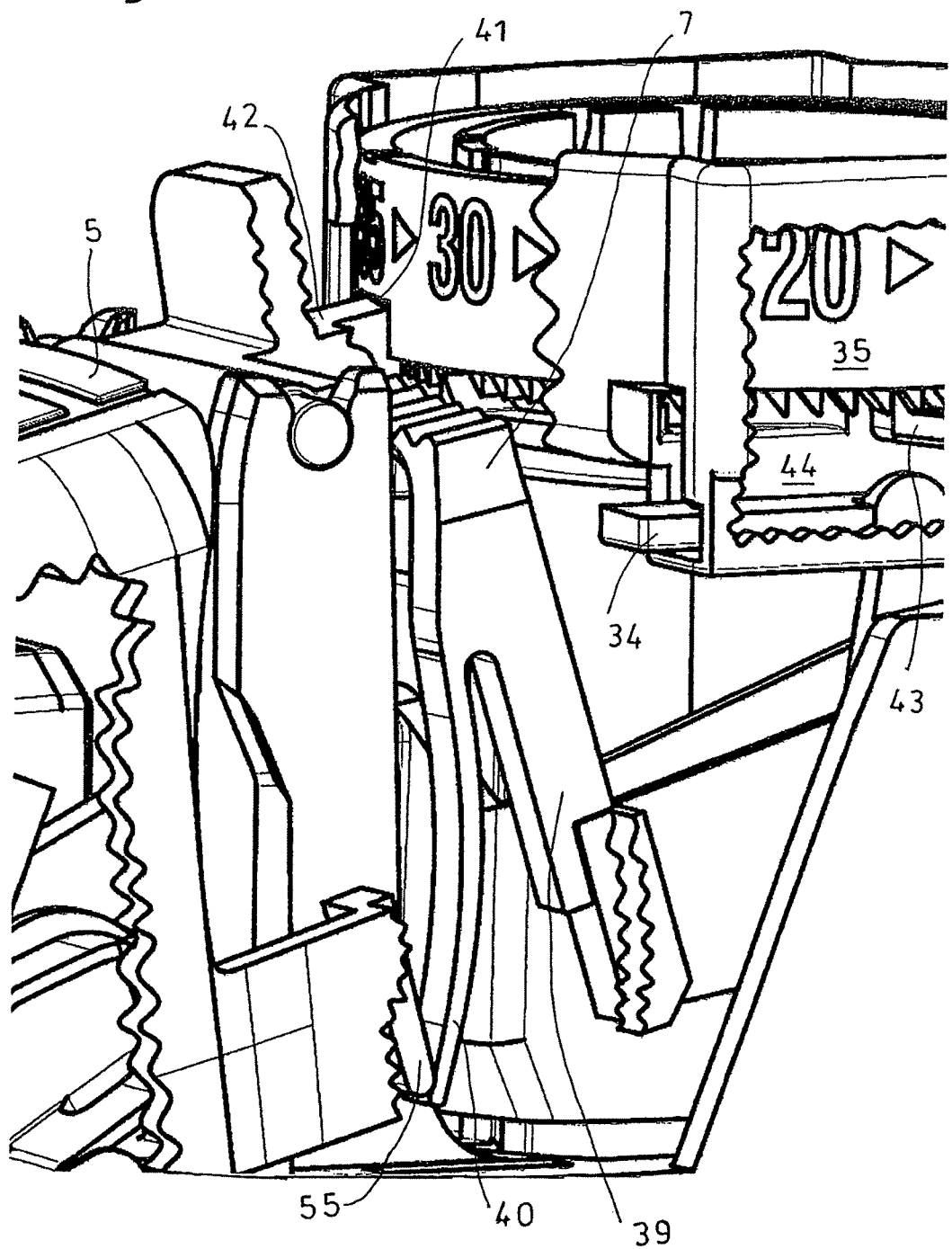

In the following the invention is disclosed by way of example with reference to accompanying drawings in which:

FIG. 1 shows a perspective view of an embodiment of an inhalation device according to the invention with the mouthpiece cap opened, FIG. 2 shows an exploded view of the inhaler according to the invention, FIG. 3 shows a partial longitudinal cross-sectional view through an inhaler according to a first embodiment of the invention, FIG. 4 shows another longitudinal cross-sectional cut through the inhaler according to the first embodiment of the invention, FIG. 5 shows a perspective view of a dosage key according to the invention, FIG. 6 shows a cross-sectional view of the inhaler in a non-actuated state of the dosage key, FIGS. 7a, 7b show a cross-sectional view corresponding to the view shown in FIG. 6 where the dosage key is partially pressed, FIG. 8a shows a cross-sectional view according to FIGS. 6 and 7 where the dosage key is fully depressed, FIG. 8b shows a perspective view demonstrating the engagement of the dosage lever into the flap valve, FIG. 9 shows a perspective view of a dosage lever of the inhaler according to the present invention, FIG. 10 shows a perspective view of a first preferred embodiment of an inhalation-operated valve closing the air duct of the inhaler according to the invention, FIG. 11a shows another perspective view of the inhalation-operated valve according to FIG. 10, FIG. 11b shows a perspective rear view of an inhalation-operated valve according to a second preferred embodiment, FIG. 12 shows a perspective side view of the inhaler according to the invention without its housing, FIG. 13 shows an enlarged detail of FIG. 12 as a rear view, FIG. 14a shows an enlarged detail of the engagement between the dosage lever and an inhalation-operable flap valve of the inhaler according to a first preferred embodiment of the invention, FIG. 14b shows an enlarged detail of the engagement between the dosage lever and the flap valve according to the first preferred embodiment, FIG. 14c shows an enlarged detail of the engagement between the dosage lever and the flap valve according to a second preferred embodiment, FIG. 15 shows another longitudinal sectional view through the inhaler, FIG. 16 shows a perspective view of a powder cartridge of the inhaler according to the invention, FIG. 17 shows a perspective view of the inhaler housing, FIG. 18 shows a detail of the counter slide gliding over the counter ring's tooth, FIG. 19 shows a detail of the cartridge's locking ratchet (locking lever not displayed), FIG. 20 shows a detail of the locking lever and its engagement with the dosage key and the counter ring.

The inhaler 1 shown in FIGS. 1 to 20 is an inhaler for powdered medicaments, for providing a large number of doses of a pharmaceutical powder medicament from a receptacle in the form of a powder cartridge. The powder cartridge 3 defines a reservoir 2 for receiving a large number of doses of a pharmaceutical powder/powdered drug. In the described embodiment, the typical number of doses which may be obtained from one powder cartridge 3 may be in the range of 30 to 60 doses.

The reservoir 2 is sealingly covered by a lid 4 as can be seen from FIG. 2. The lid is secured to the cartridge body 3a in the assembled state of the inhaler in a non-removeable fashion.

The powder medicament can be received by a patient by means of an air stream caused by the user, i.e. induced by suction. Therefore, the inhaler further comprises an activating device for manual engagement by the patient in the form of a dosage key 5 being connected to a transportation mechanism including a dosage lever 6 and a locking lever 7. The dosage lever 6 acts on a dosage slide 8 as a metering means being moveable from a filling position for receiving a powder dose into an emptying position for releasing said powder dose into a powder groove 16a of a cyclone 16 for deagglomeration of the powder in the cyclone 16. From the powder groove 16a the patient can inhale the powdered drug through a mouthpiece 10 via an air stream generated by the patient. If not in use, the mouthpiece 10 is protected from dirt by a mouthpiece cover 11. The mouthpiece cover 11 is secured to the inhaler housing fixedly, i.e. non-detachable.

The powder groove 16a of the cyclone 16 forms a part of a powder channel through the cyclone 16 which functions as a disintegration means as this is known from the art. The powder medicament to be received by the patient may be in form of an adhesive mixture. Adhesive mixtures consist of relatively large crystals, generally α-lactose-monohydrid, carrying the micronised drug particles on their surface. In the disintegration system, the dry powder will be deagglomerated for releasing the drug particles from the powder formulation. The cyclone 16, i.e. the disintegration means, generally includes an air circulation chamber as well as several air supply channels which enter the circulation chamber tangentially so that a circular air flow pattern is created inside the circulation chamber. So the total respiratory flow through the inhaler does include a transportation airflow for traversing the powder dose in the powder groove and dragging the powder into the circulation chamber, a cyclone air flow which tangentially enters the circulation chamber as well as eventually a bypass airflow for creating a so-called sheath flow of clean air. A possible design for the disintegration means is for instance disclosed in the international patent publication WO 03/000325 the disclosure of which is herewith fully incorporated by reference. The disintegration means in the following in a rather simplified form is referred to as a cyclone. In a also rather simplified form in the following the air path from the powder groove 16a to the mouthpiece opening is referred to as powder channel. It is, however, to be understood that the term "powder channel" does not necessarily refer to one distinct single powder channel but rather to a channel system as explained above.

As this can be taken from FIG. 2, the inhaler 1 includes a three-part housing comprising shells 12 and 13 as well as cover 14 received on the shells 12 and 13 via snap-fit connection in a non-releasable fashion.

The heart of the inhaler 1 is formed by a valve chamber 15 including the cyclone 16 and a cartridge body 3a.

Manual operation of the inhaler 1 by a patient functions via dosage key 5 which on depression by the patient against the biasing force of a dosage key spring 17 acts on a dosage lever 6 which is connected to the dosage slide 8 (see FIG. 15).

Dosage slide 8 is slidably moveable within dosage slide passage 18 extending below the reservoir 2 within the cartridge body 3a, as this for instance can be seen from FIG. 15.

The dosage slide 8 (metering means) includes a dosage cavity 19 for receiving a metered dose of a powdered drug.

It should be mentioned that the cartridge body 3a not only defines the reservoir 2 for receiving the powdered drug but also defines a dosage slide passage 18 extending below the reservoir 2 as well as a housing for receiving counting and indexing means as this is described hereinafter more detailed.

The dosage slide 8 is shown in FIG. 15 in its emptying position where the dosage cavity 19 is aligned with an opening 20 in the valve chamber 15 communicating with the powder groove 16a of the cyclone 16. The dosage slide 8 is moveable via dosage lever 6 between a filling position where the dosage cavity 19 is aligned with an opening 21 of the reservoir 2 within the cartridge body 3a and an inhalation/emptying position. In the filling position, the dosage cavity 19 receives a metered quantity of powder. Upon actuation of the dosage key 5, the dosage slide 8 will be advanced into the position shown in FIG. 15, thereby releasing the powder dose into the powder groove 16a through the opening 20.

In this position shown in FIG. 15, the inhaler is ready for inhalation. In the event the patient applies suction via mouthpiece 10, this forces a flap valve 22 at the very end of an air duct 9 to swing open so that an air flow can freely circulate from the open end of the air duct 9 into a powder channel defined by the valve chamber 15 and the powder groove 16a of the cyclone, into the mouthpiece. The flap valve 22 includes the flap 22a and a shaft 22b which are in the disclosed embodiment integrally formed.

The flap valve 22 according to a first embodiment in more detail is shown in FIGS. 10 and 11a. The shaft 22b of the flap valve 22 at its ends is pivot mounted within valve chamber 15.

As this can be seen also from FIG. 15, in the inhalation position the flap valve 22 is engaged by a fastening hook 23 of the dosage lever 6.

A rear side view of the flap valve 22 is for instance shown in FIG. 10. The flap 22 has an angled/bent profile including three legs 22c, 22d and 22e, the first leg 22c in the mounting position being inclined towards the closing direction of the flap valve 22, the second leg 22d being inclined rearwardly and the third leg 22e extending in forward direction and approximately tangentially to the rotary movement of the flap valve 22.

On the rear side of the first leg 22c of the flap 22a, a latching rib 47 is provided which may be engaged by the fastening hook 23 of the dosage lever 6 in the inhalation position. The fastening hook 23 at its leading end is provided with a barbed projection 50 which has a sloping face 51. The flap valve 22 includes a flap valve lever 31 integrally formed with said shaft 22b. The distal end of the flap valve lever 31 is provided with a deflector surface 53. Upon actuation of the dosage key 5 and subsequent actuation and downward movement of the dosage lever 6, a corresponding deflector surface 53' of a latch 29 integrally formed with the hook 23 of the dosage lever 6 gets into abutment with the deflector surface 53 of the flap valve lever 31. The flap valve lever 31 as well as the hook of the dosage lever are thereby both being slightly deflected, i.e. bent aside and snap back in their initial position upon further downward movement of the hook 23 of the dosage lever 6. Upon further downward movement of the hook 23, the sloping face 51 of the barbed projection 50 abuts one edge of the latching rib 47. Thereby the hook 23 is bent aside due to the resilience of its material and snaps back behind the latching rib 47 in its end position thereby engaging the flap valve 22 and being releasable by an inhalation-triggered pivoting movement of the flap valve 22.

As this can particularly seen from FIG. 14b, which shows an enlarged longitudinal cut through the flap 22a, the barbed projection 50 of the hook 23 engages the latching rib 47. When the inhaler 1 is ready for inhalation, the latching rib 47 includes a curved bearing surface 54 facing the barbed projection 50. The bearing surface 54 which defines a cam surface almost providing line contact between the barbed projection 50 of the hook 23 and the latching rib 47 so that the contact force between the latching rib 47 and the hook 23 is almost independent from the tolerances of the components. To be more specific, the planar surface of the barbed projection 50 of the hook engages the curved bearing surface 54 only tangentially so that in effect excursion of the contact surface due to tolerances of the parts of the inhaler is only possible in axial direction, which, however, has no impact on the required triggering forces. Due to this design the required triggering forces are only subject to minor variations so that triggering of the flap valve 22 is fairly reproducible. It is readily apparent from FIG. 15 that if the flap 22a moves in clockwise direction, the hook 23 is released almost instantaneously. As a result, the dosage lever may swing upwards driven by the force of the dosage lever spring 25. This upward movement will cause the dosage slide 8 to return to its powder receiving position.

Another embodiment of the flap valve 22 is shown in FIGS. 11b and 14c. Same parts of the flap valve 22 are denoted by the same reference numerals.

The flap valve 22 according to this embodiment comprises a relatively simple flat flap 22a which is not bent or angled in itself.

As this can be taken from FIG. 14c, the fastening hook 23 engages the shaft 22b of the flap valve 22 when the inhaler 1 is ready for inhalation.

The shaft 22b of the flap valve 22 (see for instance FIG. 11 b) has a cut out area 24 which is arranged approximately in the middle of the shaft 22b such that, if the flap 22a swings open (in FIGS. 14c and 11b in clockwise direction), the fastening hook 23 of the dosage lever 6 tangentially engaging the shaft 22b approximately in the middle of the shaft 22b, will be released so that the dosage lever 6 driven by the force of the dosage lever spring 25 may return to its initial position, thereby moving the dosage slide 8 back into the filling position for receiving a powdered dose from the reservoir/powder cartridge. Upon actuation of the dosage key 5 the dosage lever 6 will be moved downward while partially pivoting the flap 22a by contact of the latch 29 of the dosage lever 6 with the flap valve lever 31. After partially pivoting the flap valve 22 swivels back to its starting position by the force of its molded, integrally formed spring 32. The pivot motion of the flap 22a caused by the contact of the latch 29 with the flap valve lever 31 allows the latch 29 to engage behind the mechanical stop 30 of the flap valve lever 31 upon early release and upward movement of the fastening hook 23.

In the area of the cut out portion 24 of the shaft 22b, the shaft 22b has only a semi-circle cross-section, the leading end of the fastening hook 23 engages the remainder of the cross-section of the shaft only tangentially and only in a very limited surface area (line contact) so that the contact force between the shaft 22b and the fastening hook 23 is almost independent from the tolerances of the components. Due to this design, in particular due to the fact that a planar contact surface of the fastening hook 23 contacts a curved surface area of the remainder of the cross section of the shaft 22b, the required triggering forces are only subject to minor variations so that triggering of the flap valve 22 is fairly reproducible. Only a slight rotation/pivoting movement of the shaft 22b and the flap 22a will set the fastening hook 23 free so that the dosage lever 6 may swing upwards driven by the force of the dosage lever spring 25, thereby finishing the inhalation cycle.

A perspective view of the dosage key 5 is shown in FIG. 5. The dosage key 5 is held in its initial position/starting position by dosage key spring 17 which abuts a tongue member 26 integrally formed with the dosage key 5.

Said dosage key 5 includes an actuator blade 27 being formed as a flexible arm/leg also integrally formed with the dosage key 5 and extending downwards in the mounting position shown in FIG. 5. As this can be seen from the operating sequence shown in FIGS. 6 to 8a, valve chamber 15 is provided with a beveled edge 28 forming a kind of cam surface for the actuator blade 27 upon depression of the dosage key 5.

FIG. 6 shows a cross-sectional cut through the inhaler 1 where the dosage key 5 is in its not-operated starting position. The actuator blade 27 in this state is not engaged with the transportation mechanism, i.e. with the dosage lever 6.

Upon depression of the dosage key 5, the actuator blade 27 moves downwards and engages the beveled edge 28 of the valve chamber such that the actuator blade 27 due its inherent flexibility is deflected/bent from a first position shown in FIG. 6 to a second position in FIG. 7a where it engages at the same time the dosage lever 6. By a further movement of the dosage key 5 and the actuator blade 27, the actuator blade 27 urges the dosage lever 6 downwards against the biasing force of dosage lever spring 25. Upon full depression of the dosage key 5, which is shown in FIG. 8a, actuator blade 27 snaps back in its non-deflected and disengaged position. In this position the fastening hook 23 of the dosage lever 6 engages the latching rib 47 of the flap valve 22 as this is also shown in FIG. 8a. The device/inhaler is now ready for inhalation.

In the following the double dosing prevention mechanism of the inhaler according to the invention will be described, first referring to the first embodiment of the flap valve 22 according to the invention.

As this has been mentioned before, the dosage lever 6 in the area of its trailing end (left hand side in FIG. 9) is provided with latch 29. Upon downward movement of the dosage lever as a result of the actuation of the dosage key 5, first of all the complementary deflection surface 53' of the latch 29 gets into abutment with the deflector surface 53 of the flap valve lever 31. As a result, the flap valve lever 31 is bent aside/deflected while being passed by the fastening hook 23 and snaps back into its initial position upon further downward movement of the dosage lever 6, which ultimately will result in engagement of the hook and the latching rib 47.

It is again referred to FIG. 9 which shows a perspective view of the dosage lever 6. In the area of its trailing end (left hand side in FIG. 9), the dosage lever 6 is provided with a latch 29 for engaging a mechanical stop 30 of a flap valve lever 31 integrally formed with said shaft 22b on a return movement of the dosage lever 6.

In the event the dosage key 5 will be pressed and released too early, i.e. prior to the engagement of the fastening hook 23 into the latching rib 47 of the flap valve 22, latch 29 of the dosage lever 6 upon upward movement of the dosage lever 6 will abut said mechanical stop 30 of the flap valve lever 31. Accordingly, the dosage lever 6 locks into the flap valve 22 in a middle position. This middle position lock provides a double dosing prevention mechanism. In this middle position lock, i.e. first locked position, the relationship of lever is such that the forces required for releasing the dosage lever 6 can not be brought up simply by inhalation. If the dosage lever 6 does not lock into flap valve 22 in the end position, e.g. when the dosage key 5 is not pressed all the way down, the dosage lever 6 will not return to its initial starting position, i.e. will be locked in the middle position. Accordingly, no additional powder dose will be released from the reservoir 2. The dosage lever 6 and the dosage slide 8 will only return into their starting position after inhalation-triggered actuation of the flap valve 22, thereby releasing the fastening hook 23 of the dosage lever 6.

A double-dosing prevention mechanism is also provided with the design of the flap valve 22 of the second embodiment according to FIG. 14c. Upon actuation of the dosage key 5, the dosage lever 6 will be moved downward while partly pivoting the flap 22a by contact of the latch 29 of the dosage lever with the flap valve lever 31. After partly pivoting the flap upon downward movement of the dosage lever, the flap valve 22 will return into its closed position due to the resilience of a spring 32 integrally molded with the flap valve 22. Latch 29 of the dosage lever 6 upon an early upward movement of the dosage lever 6 will abut the mechanical stop 30 of the flap valve lever 31. Accordingly, the dosage lever 6 locks into the flap valve 22 in a middle position.

Dosage lever 6 includes a cam-like actuating element 33 which upon each actuation moves a counter slide 34 of the cartridge so that a counter ring 35 of the cartridge is moved by one count towards a lower dose. The degree of the cartridge's content is accordingly visible in a display window 36 of the cartridge body 3a indexing the fill status of the cartridge. Details of the counter slide 34 acting on the counter ring 35 may be taken from FIG. 18. Counter ring 35 which is designed as a ratchet ring with teeth 37 is rotably inserted into a collar of the cartridge body 3a. Upon actuation of the dosage lever 6, the actuating element 33 moves the counter slide 34, the counter slide engaging the counter ring's teeth 37, thereby moving the counter ring 35 so that the next index number is indicated in the display window 36. The counter ring 35 for instance provides a visual indication of a dose count for each $5^{th}$ dosing step/metering cycle. The counter ring for instance shows thirteen numbers and indicates a countdown from 60 to 0 upon each metering cycle. Each tooth of the counter ring 35 represents one metering cycle.

As this also can be taken from FIG. 4, the counter slide 34 includes a pawl 43 integrally formed with the counter slide 34. The pawl 43 is biased towards the counter ring 35 that it firmly engages the teeth 37 of the counter ring 35. The teeth 37 are unsymmetrical insofar as they have one sloping flank and one vertically extending flank, the sloping flank representing the leading flank with respect to the rotational direction of the counter ring 35.

The counter slide 34 is moveable back and forth within a sliding channel 44 of the cartridge body 3a. The cam-like actuating element 33 of the dosage lever 6 extends into the sliding channel 44 and into a recess 45 of the horizontally extending part of the counter slide 34. Engagement of the actuating element 33 with the counter slide 34 transforms a pivoting movement of the actuating element 33 into a linear movement of the counter slide 34.

Upon depression of the dosage key 5, the dosage lever will be pivoted such that the actuating element 33 is pivoted towards the left hand side in FIG. 4. At the same time, the lower leading end 46 of the dosage lever (see FIGS. 9 and 12) pushes the dosage slide 8 into its emptying/inhalation position. The counter slide 34 is thereby moved in the opposite direction. While the counter slide 34 fulfills this movement, the pawl 43 engages the vertical flank of the respective tooth 37 of the counter ring, moving the counter ring one count/step. After release of the dosage lever 6, the counter slide 34 will be moved backwards into its starting position. Due to the resilience of the pawl 43, the pawl may glide over the sloping flank of the respective tooth, thereby snapping back behind the tooth. As this can be seen from FIG. 19, the counter mechanism includes a locking ratchet 38 engaging the counter ring teeth 37. Due to the geometry of the teeth 37, the locking ratchet 38, which is also a resilient member, blocks an anti-clockwise rotation of the counter ring 35.

As this can be seen from FIG. 12, the inhaler 1 includes a locking lever 7 which is pivotably mounted in the valve chamber 15 between dosage key 5 and dosage lever 6. The locking lever 7 includes a blocking arm 39 and a spring leg 40. During assembly of the powder cartridge 3, the locking lever 7 is pushed downwards, the blocking arm 39 and the spring leg 40 thereby being moved backwards. In this position, the dosage key 5 may be freely moved downwards against the biasing force of the spring leg 40 as shown in FIG. 12.

The dosage key 5 is also freely moveable against the biasing force of the dosage key spring 17 as shown in FIG. 15.

The counter ring 35 includes a notch 41 being engageable by a tongue 42 of the locking lever 7. The tongue 42 of the locking lever 7 serves as signaling means in the sense of the instant application.

The notch is arranged on the counter ring 35 such that, after a pre-determined number of doses has been delivered, the locking lever 7 engages the notch in the counter ring with a pivoting movement caused by the action of spring leg 40 actuated by the dosage key 5. Upon upward movement of the locking lever 7, the blocking arm 39 of the locking lever 7 is pushed forward (towards the mouthpiece 10) and engages the dosage key 5 in its lowest position such that the dosage key 5 stays blocked in its lowest position after the last inhalation. It is impossible to perform another activation of the empty device.

As this can be seen from FIGS. 5 and 20, the dosage key 5 includes an actuation rib 55 acting on the spring leg 40 only while being in depressed condition in order to avoid fatigue of the spring leg 40. The spring leg 40 is accordingly only biased if the dosage key 5 is being pressed or held downward.

Apart from the indexing means in the form of the counter ring, the device includes another inhalation control window 48 indexing whether the device is ready for inhalation or not. The inhalation control window shows for instance a green-colored flag in the event the device is ready for inhalation. This is because in the activated status of the inhaler 1 a green colored tab 49 of the dosage lever 6 covers a red colored flag in the inhalation control window 48. The reset of the device from the inhalation position into the starting position takes place during inhalation by means of an airflow upon inhalation. Flap valve 22 is deflected thus releasing the dosage lever 6 as this has been described in detail before.

In order to ensure leak tightness of the air duct 9, the shells 12 and 13 may be sealed against valve chamber 15 by means of one or more sealing ribs which extend around valve chamber 15. The sealing rib may be in form of a thermoplastic elastomer which has been co-injection molded with valve chamber 15. Alternatively, the sealing rib 52 may be designed as a resilient ring which has been mounted into a sealing groove during assembly of the inhaler.

In a particularly preferred embodiment of the inhaler according to the invention, the shells 12 and 13 are sealed against the valve chamber by a labyrinth seal which completely extends around the valve chamber 15, so that the valve chamber 15 including the cyclone 16 and the powder groove 16a is effectively sealed against the dosing compartment of the inhaler. The labyrinth seal is provided by a sealing rib 52 completely extended around the valve chamber 15 and in the assembled state of the inhaler 1 engaging a corresponding sealing groove in the shells 12 and 13. This sealing assists in keeping the triggering forces for the flap valve 22 as reproducible as possible. The bandwidth for the required triggering forces normally corresponds to an air flow variation of 30 l/min for the suction to be applied by the patient. Sealing the valve chamber of the inhaler 1 against the shells 12, 13 remarkably reduces this variation in required air flow for triggering the flap valve 22. Accordingly, this design avoids the possibility of sucking an air flow through the inhaler which bypasses the powder channel and/or the air duct 9.

REFERENCE NUMERALS 1 inhaler
2 reservoir
3 cartridge
3a cartridge body
4 lid
5 dosage key
6 dosage lever
7 locking lever
8 dosage slide
9 air duct
10 mouthpiece
11 mouthpiece cap
12, 13 shells
14 cover
15 valve chamber
16 cyclone
16a powder groove
17 dosage key spring
18 dosage slide passage
19 dosage cavity
20 opening
21 opening
22 flap valve
22a flap
22b shaft of flap valve
22c first leg of flap valve 22d second leg of flap valve
22e third leg of flap valve
23 fastening hook
24 cut-out portion
25 dosage lever spring
26 tongue member
27 actuator blade
28 beveled edge
29 latch
30 mechanical stop
31 flap valve lever
32 spring of flap valve
33 actuating element
34 counter slide
35 counter ring
36 display window
37 teeth
38 locking ratchet
39 blocking arm
40 spring leg
41 notch
42 tongue
43 pawl
44 sliding channel
45 recess
46 leading end of dosage lever
47 latching rib
48 inhalation control window
49 tab
50 barbed projection
51 sloping face
52 sealing rib
53 deflector surface
53' deflector surface
54 bearing surface
55 actuation rib

What is claimed is:

1. An inhalation device for powdered drugs to be received by a patient by an inhalation-caused air stream, comprising:
at least one powder reservoir,
metering means for repeatedly metering a powder dose from the reservoir,
a transportation mechanism for moving said metering means from a filling position for receiving a powder dose into an emptying position for releasing said powder dose into a powder channel,
at least one activating device for manual operation by the patient, said activating device being operatively connected to said transportation mechanism such that upon operation a single powder dose is being metered, said activating device comprising a dosage key acting on said transportation mechanism when pressed by the patient, and
an advancing mechanism for advancing a counter means each time the inhalation device has been activated by the patient so that a powder dose has been released into the powder channel,
wherein the counter means comprises a mechanical index coupled with a locking lever which moves to a blocking position which blocks operation of the dosage key and/or the activating device and/or the transportation mechanism after a predetermined number of metering cycles after detection of the index,
wherein the locking lever blocks operation of the dosage key and/or the activating device and/or the transportation mechanism when in the blocking position by positive engagement of a blocking portion of the locking lever with the dosage key and/or the activating device and/or the transportation mechanism, respectively,
wherein the locking lever includes signaling means, the signaling means engaging the mechanical index after said predetermined number of metering cycles, the signaling means being a contour or profile coming into positively locking engagement with the mechanical index of the counter means after said predetermined number of metering cycles, thereby triggering said locking lever, and
wherein the locking lever is provided by a single piece body which includes the blocking portion and the signaling means of the locking lever.

2. The inhalation device according to claim 1, wherein the mechanical index is formed by notch or cam engaging the locking lever after said predetermined number of metering cycles so as to allow a pivot movement of the locking lever such that the locking lever comes into positive engagement with the dosage key and/or the activating device and/or the transportation mechanism.

3. The inhalation device according to claim 1, wherein the locking lever comprises an integrally formed spring leg biasing the locking lever into engagement with the index after said predetermined number of metering cycles.

4. The inhalation device according to claim 3, wherein the spring leg is only loaded while the dosage key is being depressed.

5. The inhalation device according to claim 3, wherein the dosage key comprises an actuation means, in particular an actuation projection acting on the spring leg while being pressed.

6. The inhalation device according to claim 1, wherein the locking lever positively engages the dosage key in the blocked condition of the inhalation device.

7. The inhalation device according to claim 6, wherein in the blocked condition of the inhalation device the dosage key is being arrested in a depressed state, thereby indicating the blocked state of the inhalation device.

8. The inhalation device according to claim 1, wherein the advancing mechanism comprises at least one counter slide engaging a counter ring carrying visual information on the number of doses already administered and/or still available, a translatory reciprocal movement of the counter slide causing a stepwise rotary movement of the counter ring.

9. The inhalation device according to claim 8, wherein the counter slide comprises an integrally formed pawl engaging drive teeth of the counter ring.

10. The inhalation device according to claim 8, further comprising a locking ratchet preventing bidirectional rotation of the counter ring.

11. The inhalation device according to claim 8, wherein the advancing mechanism is integrated into a cartridge body defining the powder reservoir.

12. The inhalation device according to claim 11, wherein the advancing mechanism is integrated into a cartridge body defining the powder reservoir.

13. An inhalation device for powdered drugs to be received by a patient by an inhalation-caused air stream, comprising:
at least one powder reservoir,
metering means for repeatedly metering a powder dose from the reservoir,
a transportation mechanism for moving said metering means from a filling position for receiving a powder dose in an emptying position for releasing said powder dose into a powder channel, at least one activating device for manual operation by the patient, said activating device being operatively connected to said transportation mechanism such that upon operation a single powder dose is being metered, said activating device comprising a dosage key acting on said transportation mechanism when pressed by the patient, and an advancing mechanism for advancing a counter means each time the inhalation device has been activated by the patient so that a powder dose has been released into the powder channel, wherein the advancing mechanism comprises at least one counter slide engaging a counter ring carrying visual information on the number of doses already administered and/or still available, a translatory, linear reciprocal movement of the counter slide causing a stepwise rotary movement of the counter ring.

14. The inhalation device according to claim 13, wherein the counter slide comprises an integrally formed pawl engaging drive teeth of the counter ring.

15. The inhalation device according to claim 13, further comprising a locking ratchet preventing bidirectional rotation of the counter ring.

* * * * *